US009359644B1

(12) United States Patent
Chance et al.

(10) Patent No.: US 9,359,644 B1
(45) Date of Patent: *Jun. 7, 2016

(54) METHODS OF IDENTIFYING GENETIC MUTATIONS ASSOCIATED WITH CHARCOT-MARIE-TOOTH NEUROPATHY TYPE 1C

(75) Inventors: Phillip F. Chance, Seattle, WA (US); Valerie A. Street, Seattle, WA (US); Jeff D. Goldy, Seattle, WA (US); Thomas D. Bird, Lake Forest Park, WA (US)

(73) Assignee: University of Washington, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/245,591

(22) Filed: Oct. 3, 2008

Related U.S. Application Data

(62) Division of application No. 10/756,194, filed on Jan. 13, 2004, now Pat. No. 7,449,291.

(60) Provisional application No. 60/440,399, filed on Jan. 13, 2003.

(51) Int. Cl.
*C12Q 1/68* (2006.01)

(52) U.S. Cl.
CPC ........ *C12Q 1/6883* (2013.01); *C12Q 2600/156* (2013.01); *G01N 2800/28* (2013.01)

(58) Field of Classification Search
None
See application file for complete search history.

(56) References Cited

U.S. PATENT DOCUMENTS

| 6,432,640 B1 | 8/2002 | Polyak | |
| 6,566,501 B1 | 5/2003 | Amar | |
| 7,449,291 B1 * | 11/2008 | Chance et al. | 435/6.16 |

FOREIGN PATENT DOCUMENTS

| WO | 02/04514 A2 | 1/2002 |
| WO | 02/29103 A2 | 4/2002 |
| WO | 2005/000087 A2 | 1/2005 |

OTHER PUBLICATIONS

Young et al., 2003, CMLS, vol. 60, pp. 2547-2560.*
Sai Fi, G.M., et al., "Mutations in the SIMPLE Gene are a Relative Common Cause of Dominant Charcot-Marie-Tooth Disease (CMT1C) and Related Peripheral Neuropathies," Poster Board No. 2419, 53rd Annual Meeting of the American Society of Human Genetics, Los Angeles, Nov. 4-8, 2003.
Sai Fi, G.M., et al., "SIMPLE Mutations in Charcot-Marie-Tooth Disease and the Potential Role of Its Protein Product in Protein Degradation," Human Mutation 25(4):372-383, Apr. 2005.
Street, V.A., et al., "Mapping of Charcot-Marie-Tooth Disease Type 1C to Chromosome 16p Identifies a Novel Locus for Demyelinating Neuropathies," Am. J. Hum. Genet. 70(1):244-250, Nov. 2002.
Street, V.A., et al., "Mutation of a Putative Protein Degradation Gene LITAF/SIMPLE in Charcot-Marie-Tooth Disease 1C," Neurology 60(1):22-26, Jan. 2003.

* cited by examiner

*Primary Examiner* — Olga N Chernyshev
(74) *Attorney, Agent, or Firm* — Christensen O'Connor Johnson Kindness PLLC

(57) ABSTRACT

In one aspect, the invention provides methods of identifying genetic mutations that are associated with peripheral neurological disease. The methods comprise identifying a difference between a nucleic acid sequence of a small integral protein of the lysosome/late endosome ("SIMPLE") gene from a mammalian subject exhibiting peripheral neuropathy and a nucleic acid sequence of a SIMPLE gene from a subject which is not exhibiting peripheral neuropathy, wherein the difference is a genetic mutation associated with peripheral neurological disease. In another aspect, isolated nucleic acid molecules encoding SIMPLE missense mutations are provided. In another aspect, a method of screening a subject to determine if the subject has a genetic predisposition to develop Charcot-Marie-Tooth type 1C neuropathy is provided. In another aspect, the invention provides kits for determining susceptibility or presence of Charcot-Marie-Tooth type 1C neuropathy in a mammalian subject.

5 Claims, No Drawings

SEQUENCE LISTING

```
<160> NUMBER OF SEQ ID NOS: 21

<210> SEQ ID NO 1
<211> LENGTH: 486
<212> TYPE: DNA
<213> ORGANISM: Homo sapiens

<400> SEQUENCE: 1
atgtcggttc caggacctta ccaggcggcc actgggcctt cctcagcacc atccgcacct      60
ccatcctatg aagagacagt ggctgttaac agttattacc ccacacctcc agctcccatg     120
cctgggccaa ctacggggct tgtgacgggg cctgatggga agggcatgaa tcctccttcg     180 tattatacc agccagcgcc catcccaat aacaatccaa ttaccgtgca gacggtctac      240
gtgcagcacc ccatcacctt tttggaccgc cctatccaaa tgtgttgtcc ttcctgcaac     300
aagatgatcg tgagtcagct gtcctataac gccggtgctc tgacctggct gtcctgcggg     360
```

```
agcctgtgcc tgctggggtg catagcgggc tgctgcttca tccccttctg cgtggatgcc      420
ctgcaggacg tggaccatta ctgtcccaac tgcagagctc cctgggcac  ctacaagcgt      480 ttgtag                                                                 486
```

<210> SEQ ID NO 2
<211> LENGTH: 161
<212> TYPE: PRT
<213> ORGANISM: Homo sapiens

<400> SEQUENCE: 2

```
Met Ser Val Pro Gly Pro Tyr Gln Ala Ala Thr Gly Pro Ser Ser Ala
1               5                   10                  15

Pro Ser Ala Pro Pro Ser Tyr Glu Glu Thr Val Ala Val Asn Ser Tyr
                20                  25                  30

Tyr Pro Thr Pro Pro Ala Pro Met Pro Gly Pro Thr Thr Gly Leu Val
            35                  40                  45

Thr Gly Pro Asp Gly Lys Gly Met Asn Pro Pro Ser Tyr Tyr Thr Gln
        50                  55                  60

Pro Ala Pro Ile Pro Asn Asn Asn Pro Ile Thr Val Gln Thr Val Tyr
65                  70                  75                  80

Val Gln His Pro Ile Thr Phe Leu Asp Arg Pro Ile Gln Met Cys Cys
                85                  90                  95

Pro Ser Cys Asn Lys Met Ile Val Ser Gln Leu Ser Tyr Asn Ala Gly
                100                 105                 110

Ala Leu Thr Trp Leu Ser Cys Gly Ser Leu Cys Leu Leu Gly Cys Ile
            115                 120                 125

Ala Gly Cys Cys Phe Ile Pro Phe Cys Val Asp Ala Leu Gln Asp Val
        130                 135                 140

Asp His Tyr Cys Pro Asn Cys Arg Ala Leu Leu Gly Thr Tyr Lys Arg
145                 150                 155                 160

Leu
```

<210> SEQ ID NO 3
<211> LENGTH: 37775
<212> TYPE: DNA
<213> ORGANISM: Homo sapiens

<400> SEQUENCE: 3

```
gtttctctcc ctgccccgc  gacttcgcgc aagatccggg aaggacaccc gaggcccctg       60
ggagaccctg gggaggtgaa aatcagagag cgaagcgggc cgtggcccct aggcctgacc      120
cctccccgcg gggtaaggcg ggcaccccgc gagcgcaggg gtcctcttac tgctgatggc      180
acccagctct gggcccagac gccgctcacc gtccaccgcc ggtgctgggt aggtgctggt      240
gggaccagct ggtgactggt ggcagaagtg gatctcgccc ctccctgcca agctaggcaa      300 atacccctcccc cgctctggtt tgcaggtcac tgtggatagg tggtcagttg gtggtgtgcc      360
cgaagctctt cggggtcagg gagaggaggt gatagcggaa aggtgtatgt tctggaaggg      420
ccagtcatgc ttcagggacc aggctagttg gaccttcact ggttttctac ttcccgacag      480
tggagctgat gtcactggct gttggactga gcagtggtca ctgggaaatc tacagtttgt      540
ggaagccacg gggtcttcca agctcctacc agtcttccca aagaggatgc ctccctcccc      600
ttggcctggt gcactggtgc tggttcaaag actgtctgaa gcccagcttg ggtcctctt       660 taggaaagcc atgatttgcc ttaatgtgtg cttggctgct tcatctgccc tctcacccccc     720
```

```
tgccttctca gagtgactct ttttaggact tcctatttag gactaaccca gatgcctaca      780
gagagaagtg caggctggta tctggaattc caccagtgtt ttggttttat cagttggagc      840
aggatctaga tggcgtgtga cttgctttac ctggcataga gtaaccccca tattgcactt      900
ggctttcttc tccaccagcc cttgctctgg gaactaaatg tgcaccaaac tctctaagaa      960
acatttaatt gtaatctacc atgagggagg cccatctccc tctttcctgt tactttaagg     1020
catgaataat tgatgcattt attcacattt gagaaagtat cttgtaatgt tttcacagat     1080
taagtgactg ggtgattgat ctaagacgta ggatcaattt ctttcttttt tttttttttt     1140
tttgagacag agtctcactg tcgcctaggc tggagtgcag tggtgcgatc tcggctcact     1200
gcaacctcta accctcccca ccccacctca acccctgcc tgagttcaag caattctagt      1260
gtctcaacct cccaagtagc ggggattaca gttgggtgcc accatgctta ggtaattttt     1320 gcattttag tagagacaga gttttgccat gttggccagg ctgttttcga acttctgacc       1380
tctagtgatc cacctgcctt ggcctcccaa aatgctggga ttacaggtgt gaactacctc     1440
acccggccca tttcttaagt ctctaaaata gtagattgaa gtgtaattca ctgtctttgg     1500
ggaatacatt tcccttttgtt acttccgttc cttttatggg cgggctgttg agaaataaag    1560 cgctacccctt gccgtgtaaa ggatgcagaa gaatggctcc tggtcctgag gggtttacgc    1620
aatgggtaga aagtagaaac acacaccggc gaaaagctg gtgcttgcta atgcccttgt      1680
aactccagaa agggcttgag aacagtgaa aggaggcagc taagttagag aaagtttcat      1740 ggaaaactg aggcctgagc acatgtggca gaaggaacat gaggacatag ttcagacaaa      1800
caggagggtc tcagtagagc tgtggaagag gtacagacaa gcccaggtgg ttgaagacag     1860
taaatggaaa atccactgag aggaaggagc tggaaggcgt ttccagcccca agttaatttt    1920 caagaaaata aacagtgcat attttgctga cattacccat cctcactgct cagaggtgta     1980
taatagcact ttgagaatgg gctggtgccg ttttgtgact taaacttctc ccactgaata     2040
ggaatttccc cagagctaca gtgagggtgg aaaaagagg atctgcaaga ggaagtcctg      2100
tattcttggc actgtgactt gtcctctatt tgttttcgct tttacagcag tgaaaatagc     2160
cccgtgggtg aggcggtcta tcaggtaaat agacttcctt agttctgtgt ttcttttagca    2220 cacatatttt tgacgtctcc cgggtctgtt tggccaccca tggtctgttc tgaatttgat     2280
tgatgtttac ttgcctaaga attgttattt gaggtcaagt ggcattttcc agggtcctca     2340
taatttcatc ttgttgtttg agcctgtatt gattgacact ctggacacag gtgacaacag     2400
ctttgtagct aatgaagttg tccccttggct gcaggttatt tcagtagaag aattgtgtaa    2460
tttcatagag cttaaggcat ggacacaaga aaggaaccat tctggagggt gtctatgtga    2520
tggtaattct ctgctcacct cgcagtaggt aggagtttat ataccaggat ccaaagctgg     2580
aggcttcaga gaaataatg ttggagaatt taagctattt agctcatgga gccttagatt      2640
taattgacag tgtgcctcag gtaagtttaa gagcttaatg atgtcttgcc ttaaacttga     2700
atccatgagg ttattcctag atgatgcact gatagtttga aatttttat taaaaatat       2760 taaagtgtgg aagataaaga agaaaggcat aatcttatag aacgaaacaa ctaccactgg     2820
ctgtccttat cggcggctt ctgtcttttg tctttgtgcc tgttttctat gaaattgtca      2880
tcagcgttca tacaattttg tatcctaatg cagtctcagt cttattaatg atctccttgc     2940
actgtttgat gaaaaactgt gattcacgtg gaaactaggg atgtggtttc accaggagtc     3000
cagaggaaaa ctgcccactc tgattgtggg ggagcagccc aactcccga tggaagcatt      3060 ttccattcca caaatcactg tgatttgtca ttacgccatg cttgaacctg gctttaagat     3120
```

```
tgtggtaact ttatctttga cttgtgggac ataccgccct gcagaaacag cctgaactca    3180
gaagatggaa ttggcacaca tttctctgaa atatttcact ctgagcttct gtacttttac    3240
tgaggtctac tgaaactgga atttgtttgg gatcaaataa ccaaaggcca atttctcgct    3300
tcctttccca aagagctgga ggtccgggtt tccccttttg tctaccttcc tgcttaacca    3360
tttatggctt aagacgcacc attcaccttg aacattttca ggaatgatag acaggttaaa    3420
ttccatgaca acaaaaaccg tattgcagaa ttattgtagc ttaaaacctg ccaggtgacc    3480
ctccttagtt taagaatttt aagcaatatt caatttaata agtgtacaat tggatagtt     3540 cctgaaagtt gattatagtc aggatccact gtgctcccat tattggaaat aacgtttttc    3600
tccagagacc ctaaaagacc agaccttttt gaccctcgca gctggttctc tttcttgttt    3660
acaaactagg ctattttctt aggggacctg acaatttgca tgtgagtgcc cttcttttgc    3720
ctaaggaatc ccttttttta ttctggggtc atttctgcga tatacatatt catgggccta    3780
gcttagtgtt tcttttctgg gggctgggag atggagacca gagtagaatt gaatatttct    3840
cctttttctt cctggaagaa tcgatcttcg aggattaagt tggtagttaa aaagccgctt    3900
tatctttctg aaggccttgc cctttttatgt gttgatctga tacccaaatg tagaaaacag    3960
ttctatacac agcttgagga tatattttta gaagagttta ccacccacat gtggctaaag    4020
ctttgtgggg agttcttttt tttttttttt ttttccgttg tgagtgaaat agatatttca    4080
ctatatcttg ctcttgtttt caaacccttt aaaaagccat tgaccatttt ctcttttatt    4140
tttagttgac acataataat catacacatt tatgggataa agagtgatat tttcttatat    4200
gtctccagtg tgtaattgat caaagagtaa ttggcatgtt catcacctca aacacttatc    4260
atttctttgt gttgtgagca ttcagaattc tctcttctag ctatttgaaa atatacactg    4320
aataattgtt aaccatattc ccctacagt tctacagaac agtagaactt attcctccca     4380
ttgaactgta actttgtacc tatcaaccaa cctctctcta gcctctcttc ccctcccctt    4440
tgtaacctcc agtaaccaca gttctttct ctacttctgt gagctcaatt ttgtcgtcct     4500
tcctttgtgg aagctgtgaa ataccttttcg aggggagtgc ggacttgtgg tcaggtgtaa    4560
atatgcattc agctgggcag agtttgggag attcctttaa aacctgttct tttgctgaaa    4620
ttctaggtat cttttttattt tatttttattt tttatttttc acctcatcag ttagaagtgt    4680
cagaaactct cctttaccccc ccactagtc tttggcattt aaccaaaata tactttattt     4740
acttatatat ttttgagat agggccttgt tctgttggcc aggctggagt acagtggcgt     4800
gatcacagct ccatgcagcc tcaacctccc tctcgagctc aagccatcct tccacctcag    4860
ccaccacact aatttagtg gttttttgtt gtagagacag ggtttcgcca tgttacccag     4920
gctggtctca aactcttgga gtgaagtgat ccatccatct tggcctctca agtattgcc     4980 attacaggca tgagcctcac cccaaagcac tcaaattttg tttttttaaa ttgaacttga    5040
gtgctttggg gtaagacctg cctattccat ttcaccttat agttttcctt actcttggcc    5100
tatgtagggg agagagaaga ctttctttct gccttctgaa ggtaccataa ttgagcctat    5160
gaaataaact gatgatagat taacggatga aaatacatac aaatttattc catgcataaa    5220
tgtgggagtc ccacagaaag tgaaactcaa agcaaggtca gataattgaa gtttatgtag    5280
tgtgcctgag ctacgaaaaa ggaataagcg gctgggcgtg gtggctcatg cctgtaatcc    5340
cagcactctg ggaggacaag gcaggaggat cgcttgagcc caggagatca agaccagcct    5400
gggcaacatg gcaaagccct gtctctacag aaaatacaaa aattagtctg gcatggtggc    5460
```

```
tcatgcctgt gatcccagcc actctggagg ctgaggcaag aggatcgctt gagcctggga   5520
ggtcgaggct gcagtgagcc gagatagtgc caccgcactc ccgcctgagt gacagacaag   5580
accctgtctc aaaataaaaa agaaaaagga ataggggcct ggggctcctg gaggcaggtg   5640
gtgataggtt atagaagggt aaggggagga aatgtatggt gaacaaaggt tgccttgtta   5700
atgcagataa aaagcctctt gaatgatgaa agttgtctca gagtagcctc agaagagcag   5760
gtgatggctt gtgaccaggt gtcgaccttc agtctcctct cctaagttaa gatcttccag   5820
ccaggcacgg tggctcacgc ctgtaatacc agcactttgg gaggccaagg tgggtggatc   5880
atgaggtcag gagttcaaga acagcctggc caacatggtg aaaccccgtc tctactaaaa   5940
atacaaaaat tagccgggtg tggtggtggg catctgtaat cccagctact caggaggctg   6000
aggcaggaga atcacttgaa cctgggaggc agaggttaca gtgagctgag atcacaccac   6060
tgtacgccag cctgggccac agaatgagac tccgtctcaa aaaaaaaaa aacttcactg    6120 gttgatgagg gtcctatgat agtcactttc ctttacacag atcaagtatc tcttctctga   6180
aatgcttggg accggaagtg tttcagattt tggatctttt tttcagattt tgaaatactg   6240
cattctactt actggttcag catctctaat ccaaaaatcc aaaatccaga atgctccaat   6300
gagcatttcc tttgagcatc atgtctgtgt tcaaaaagtt tcagattttg gattttcaca   6360
tttgggataa tcaacctgta gatttcaatt tattgtatca aagggcagct tttcagagct   6420
gctcctgtgt ctgcagtttc tcagaataat cagctcaata tatgccaaag aaatagatcc   6480
tgaggtgaca tgttctagtc cctgcagtc ataattttggg gtagtgtgtc ctgagcccca   6540
tcacctatct gactcattta taagtgggat ccctgaaagt atttaaataa acttttaatt   6600
ttggcataat ttttgatttg caagaaagtt gtgaagttag tacagggagt tcctcaccca   6660
gttcctggtt ctctccatta ttcacatctt acatcacaca gtatgtttgt caaaccaaga   6720
aactgatgag ggtatgttat tgttcaccaa actccagact ttatctggag ttcccagttc   6780
tcccactgat gtccttttt tctgggccag ggtcctaacc tagggtacta cattgcattg    6840
atatatttta ttttattta ttttattta ttttattta ttttattta ttttattta        6900 ttttattta tttttttgaga cggagtctcg ctctgtcgcc caggccggac tgcggactgc   6960
agtggcgcaa tctcggctca ctgcaagctc cgcctcccgg gttcacgcca ttctcctgcc   7020
tcagcctccc gagtagctgg gactacaggc gcccgccacc gcgcccggct aatttttttgt  7080 attttttagta gagacggggt ttcaccgtgt tagccaggat ggtctcgatc tcctgacctc   7140
atgatccacc tgcctcggcc tcccaaactg tgttttattt ttttgagaca gagttttgtt   7200
cttgttgccc aggctgcagt gcaatggcac aatctcagct aactacaacc ttggcctccc    7260
gggttcaagc aactctcctg cctcagcctc ccgagtagct gggattacag gcacgcacca   7320
ccacacccag ctaattttg tattttttagt agagatgggg tttccccatg ttggccaggc    7380
tggtctcgaa ctcccgacct caggtgaccc accgcctcg gcctcccaga gtgctgggat    7440
tataggcatg agccactgtg cccggcccca cattgcattt agtcatcttg tctcctcagc   7500 cacccctggct atgttagttt ctcagtcttg ctttgttttt cataacctag atactttttg   7560
aagatgaggt attctgtaga atttccctca aatcagggtt gtctgatatt tttctcatga   7620
ttacagtggg gttgtgggtt ctgggaggag aagaccacgg aggtgaagtg tccttctcat   7680
cctgtcacat cagagggcac atgacatgca catgacattg cagatgttaa tatcaaggga   7740
gagagtaaag tattcctgat gttaattaat atcaagagag agagtgaaaa ggaggtattt   7800
gccagatttt ctcgcttgta gtttactgtc tttccctttt catagatgga gttttgctct   7860
```

-continued

```
tgttgcccag gctacagtgc aatggtgcga tcttggctcg ctgcaacctc tgcctcctgg    7920
gttcaagcaa ttctcctgcc tcagcctcct gagtagctgg gattacaggc atgtgcctgt    7980
atatagacat gttttcccat gttggccagg ctggtctcga actcccgacc tcaggtgatc    8040
cacccgcctt ggcctcccaa agtgccggga ttacaggcat gagccaccac gcctggcgac    8100
tctgttcttt gaaagagagt caaggagtcc agcccacaca caggagagga aagggagaga    8160
ttaaattcca cctcctacga ggtgccatgg ctcatgccta taatcccagc agttttggag    8220
gctgaggcgg gtggattact tgaacccacg agtttaagac cggcctgagc aacatattga    8280
gacccccatc tctatggaaa gttaaaaaaa aatcgctgag tgtggtggtg cacacctgta    8340
gccccagcta ctcaggaggc tgaggtggga ggatcatttg agcccaggag ttgaaggctg    8400
cagtgagtta cgatcaagcc attgcatgcc agcctggaaa tagtggaatg agcaagaccc    8460
catctctaca aaaaatagaa aattagctgg gcttgttgat gcacacctgc agtcacaact    8520
actcgagagg ctgagggagg aggatcgctt gagcccagga ggctgaggcc atagtaagct    8580
atgatggtgc caatggtgcc actgcactcc agcctgggtg acagagtgag accctgtctc    8640
aaaaaaagaa aataaaataa aagtgcatcc cctggagagg gagtatctac tcatactatt    8700
tggaatttgt cagtgaggaa gatttgtctt ttcttgttta aaaaatagac acttctggcc    8760
aggtgtggtg gcttacacct gtaatcccag cacttcggga ggctgaggtg ggtagatcac    8820
ttgaggtcat gagttcgaga ccaacctggc cagcatggtg aaacctcatc tctactaaaa    8880
gtacaaaaac tagccgggcg tggtggtggg tgcctgtaat ctcggctact cgggaggctg    8940
aggcaggaca attgcttgaa cctggaaggt ggagcttgca gtgagccgag attgtgccac    9000
tgcactccag cctgggcaac agagggagac tccgtctcaa aaaaaaaaa aaaaaaatag    9060
acacttctaa tgagctgatg ccatagatac cctgtcatag atgggataga tgtgccatat    9120
gggcacagga gacctcagct gtgcaaggat gtcagatgca cttggctttc tcaagccctc    9180
gtggggaaat atagatcaca tcccttcccc tggggtgggc agagagtaac gtaatatggt    9240
ccagttaggg aaatattaat agaagctaac ttgcagacag gaagcaatta ggatgcagga    9300
ggaagacata tgtcatcaag ggctagatca tgtggtgtca gccaggggat gtgaaacagg    9360
catgaaaagc gcttgacagg caatgtccac caccaccctg ttcccacatt atccgtaagt    9420
cttgctaaag gcaagattgc tgttttctgg aattttcaaa gacagacagt tggactacct    9480
gcagtcatct ggaatttggc cagaacaaag gaagtaagca aatagaagac tcccaaataa    9540
ggtatatatt tatcatcaaa gcagatgccc aagcctgttt acctcactca gaggaggcgc    9600
ccacggcaac tatgaactct tactttacac agagtccttg cacgctgggt tctgctggtg    9660
tccaagtcct cagaggcttt gaagtagcaa attgtgttgg tgggatggag ccgccatcag    9720
ccccatgttg gactgttggc agcctgggac cgtgtagaac cacagatgtg gacacaagca    9780
ttttccttt cctttctctt tttctctttc tctctctctt tttttttttt ttttttttg    9840
cagattgtaa gaaaggagag gggaatatgg gaatttattt atttatttac ttatttattt    9900
attttgagac agtgtcttgc tctgttgcct aggctggagt gcagtggtgc gatctcagct    9960
cactgcaacc tccacctccc aggttcaagc aattctcatg ccttagcctc tggagtaact   10020
gggactacag gcatgcacca ccttgcccag ctaattttg gattttagt agagatgggg   10080
tttcaccatg ttggccaggc tggtctcgaa ctcctgacct caagtgattc acccgcctcg   10140
gcctcccaaa gcactgggat tacaggcatg agccaccgtg cccagctggg atcgatttta   10200
```

```
gaaaaagatt aaggctgagt gcagtggctt atgcctgtaa tcccaacgct ttgggaggat   10260
cacttgaggc cagcctgggc aacatagtga gaccccgtct ctacaaaaaa ttaaaaatta   10320
aaaaaactag ctaatcatgg tggcatgtgc ctggagtccc agctggtcga gaggctgaag   10380
tgggaggatc actcgaaccc aggagttcaa ggctgtagta agctatgatt gcgccactgc   10440
actgcagcct tggcaacaca gcgagacccc gattgtaaaa caaagttcag tttaagaaag   10500
aaaaaagaaa agaaaaaggt taagatactt ttttcggggg aatgtttaca gaggctgtgg   10560
gtcagaatga agcaacacca gaagctatgg agactggggt ttctgctgtg tttcaacttg   10620
gttttttgtg ttctcgggag aagacaccct tggccgtggg ccgtgagacc tttgatgtgt   10680
gtttacgctg accgcgagtt gttgggatgg cttctgcggt gggtggttct cttggtattc   10740
tcggttttga agcttatttt tagactctga actctccttc ttggcaggag ttgaatcccc   10800
ctgggggttt tcaagttgtt cttggactgc tggttttga aatagaagcc cctttggtgg   10860 ggtccccat aaacccaggc gctggtgccc accttgtgat gtgaaggctc ctgtaacacg   10920
acctcacttt cctggccccg cactactcac ctgcccacg ggacacaggt acatggcttc   10980
tgggtgtctg tccccgctgt acccagatct gcccccttgc ccttgtcccc agatcctcca   11040
ctcgctccta ggaaccgtac ccctcccaaa acaaaaaaag aaactatacc cagtctcccc   11100
ttcatatctc tcccacatct gcccctgttg gttgactttg cctccctata tgggtcccat   11160
aaggccggca agggagggtc cacatctctc aatcctttgt ccaccattgg tgtttagaac   11220
cccctggagg aaaactggat catagtgcaa catgaaaaaa aaagaacttt aggccgggtg   11280
cagtggctca cgcctgtaat gccagcactt tgggaggccg aggtgggcgg atcacttgag   11340
gtcaggagtt cgagaccagc ctggccaaca tggtgaaacc ctgtctctac taaaaataaa   11400
aaaatgagct gagcgtggtg gcatgcacct gtaatcccag ctatttggga ggctgaggca   11460
ggagaatcgc ttgaacctgg gaggcagagg ttgcagtgag ccaaggtcac gccactgcat   11520
tccagcctgg gccacagaat gagactctgt ctcaaaaaag agaaaaaaa aactttatat   11580 tgacaaatag gatgttgtta gtgcaaattt tggggttgat atagtgggag tggtaaaggg   11640
aacgtcttct taccaaatag aaataattag aagctttaat cactctgcaa acagggaagg   11700
tcccagggcc aggtgctggg caggaacaca aagggctgtg atgacatcac ctttacccag   11760
aggcgggaag gacccaggat ggaggcctgg ggagggcaga gacaggtttg cagaggagac   11820 tttcttttt aattaaaaaa gtatgtattt tgtaaatatg taatattact atggcttaac   11880 atacaaaga ccagcaaggg tgtaaaagtg accagtgttt gtcacacccc atcccctagt   11940
ccacctggtt cccttcccga caaacaccga ccgttaagtt tcttatgtat gcctttggag   12000 acatttttg catattatat aaagaaatac taggccaggc atgatggctc atgcctgtaa   12060
tgccagcgct ttgagaggcc aaggtgggag gattgcttta gcccaggagt ttgagacaag   12120
cttggtcaac atactgagac cccgtctcta caaaaaataa aaaaattagc taggtgtggt   12180
ggtgcacacc tgtagttcta gctgctctgg aagctgaggc aggaggatcg cttgagcctg   12240
ggagctccag gctgcaatga gctatgatca tgccactgca ctccagcctg gcaacccag    12300 tgagaacctg tctttaaaaa acccagtgag aacctgtctt taaaaacaac aacaaaaaaa   12360
aaaccaaaaa aacgccgggc accttggctc atgcctgtaa tcccagcact ttgggagccc   12420
gaggcgggag gatcacttga ggtcaggagt ttgagaccag cctggccaac gtggtgaaac   12480
cccatctcta ctaaaaagac aaaaattagc tgggtgtggt ggtgggcgcc tgtaatccca   12540
gctatttggg aggctgaggt aggagaggtg cttgaacctg agaagtggag gttgcagtga   12600
```

```
gtcgagatcg cgccactgca ctccaacctg ggcaacagag caagactcct aaaaaaaaaa    12660
aaaaaaaaaa aaggatatct tcttctctca ccatacacaa atggtggcac actacaaaca    12720
ctctcctgcc tcattaaaca tgatagtata tcttggtggt gattgcattt ctccaaataa    12780
aactcttcct cgtttcagta ccttgtgggg agggaccatc cctgattggt acccttgcct    12840
tgctggcgga ctaggcttct gctgttacca gcaacgctgt agtgaatacc ccatgtgctt    12900
gtcattttgt catttcagcc acatgtgggg gttattgcca gcacacattt ctggaggaag    12960
agttgctgga cttgttcatg ttaaatttgg ttggccgttt ctgttgcagg agcctcagtt    13020
tatcgatacc caggctagct ctctgtgtgt gttaccaaca ttttgctctt tgcctggtgg    13080
atgggtgaca aatgatatca tgatatcatg gcattggtta tggggtttaa aaaaaatctt    13140
ttatggccgg gtgcagtggc tcactcctgt aaccccctggc ctttgggagg ccgaggcagg    13200
cggatcgctt gaggtcagga gtttgggacc agcctgggca acatagtgag accccatctc    13260
taccaaaaat acaaaaagtt agccaggcgt ggtggcacac gcctgtagtc ccagctactc    13320 aggggggctga ggcatgagaa ttgcttgaac ctgggaggcg gaggttgcag tgagctgaga    13380
ttgcgccact gcatgccagc ttggttgaca gagtgagacc ctgtctcaaa aaaaaaaaa    13440 agagcttgag atgtgcagaa aattggtaca attaatacag agagctccca tttactgtca    13500
cccagcatct acttccctat gggacactgg ccacaactgc ttctctgaca ccgctgcgtt    13560
actgtttacc aaactccagg ctttatttgg acatcaccag ttttttccaac taaggctttt    13620 ctgtgccggg gttctacgtt gtattcagtt gtcacctctc tattcattgt cctctggtct    13680
ctgacagttt cttggacttt cctgtttttcc gtgactttga cagttttgag gagtgctggc    13740
ctgatgccct gtggccggtt ttctcatgac tacgtggggc tgcgggttta ggggaggaag    13800
gccacagagg cccttctcac ctcatcctgt cagtcagccg gtgtgtgatg tcccgtcagc    13860
aggtgtgtga tgtcccgtca gcaggtgtgt gatgtcatgt gacttctcgc tggtgtgtga    13920
tgtcatgtga cttctcgctg acgatattca gcccgatcat ctgtctctgt gtggttttag    13980
ttgcatctcc ctgcttttga ggaggactgg agcatcattt catgcatgag gactcggggt    14040
gttgtctagg ggagggctgt ggtcagcttg atgcgtttga ggttgagggg tgggggaac    14100 cacaagggct tcgtgcagac cctgcgtacc tggggagcag gaagggaaca ggagtgtctt    14160
gacgtggaag gtggatttgg aggagaggca ggtcactgga ggggctgagg acccaggcta    14220
aggcaggagg gggattttgt tttgatctgt ttatttgttt gtttgtttat ttatttattt    14280
attttgagat agggtcttgc tctttcaccc aggcaggagt gcagtggcgt gatcacagct    14340
cactgcagcc tcaaactcct gggctcaagt gattctccca cctcagccct gtgagtaggt    14400
gggactacag gtgcgcacca ccacgcctgg ctaattaaaa aaagagacag agttttgcca    14460
ttttgctcag gctggtcttg aactcctgga ttcaagtgat ctccccacct cacctcccaa    14520
agtgctggga ctacaggcat gagccaccgt gcttggaaag attaaaccat ttaggagacc    14580
tcaggaaaag agccagccga gagggcgtga ttggcaagag gggacattgt ctgagcacag    14640
tccctcccag agaccacagg gcccactccc acctagagat ggccacattc accagattga    14700
agtttgaacc agaggaggag ggctgcttct gagcccaggc cggcagaca gatgcctggg    14760 ggttcaggtg ggaggttgag ggggtctgac ctctgcctgg tgcccctgc tgtgggaggg    14820 ggaagagtgc ccattgagaa tctgcagggc cagtggggaa tctgggcaac ccagctatga    14880
gggtggatgg atgagttttc taactcatta ccctgaactc agtggcttag gtaacgtgaa    14940
```

```
tgtagtatct tccagttctg gagcctgaag tctgcagtgg gcttcctcag attaaatgca    15000
atgtgtcgac tgggcgcagt ggctcacgcc tgtaatccca ccactttggg aggccgaggc    15060
aggcgaatca cctgaggtta gagtttgag accagcctgg ccatcatagt gaaactccat    15120
ctctactaaa atacaaaaat tagccaggca tggtgttggg tgcctgtaat cccagctact    15180
cagaaggctg gggcaggaga atcgcttgaa cctgggaggc ggaggttgca gtgagctgag    15240
atcgcactac tacactccag cctgggcgac agagtgagac ttggactcaa caacacacaa    15300
aaaatagcag tgtcagctgg actgtgctcc tggaggctcc tggggaaaat ccatggtctt    15360
gcctttccca gcttccagag gccgcctgca tttcttaatt tatggctcct tcctccccct    15420
tcaaagccaa cagcttcctt tttctacatt taaacccaac agaggtcttg ctctgttgcc    15480
caggctggag tgtagtggtg cagctgtggc tcactgcagc ctcaaccccc tagaccccac    15540
cccccaacct ccttctacct cagcctccca agtagctggg atgatacatg tgcgctatca    15600
caccttgata attttgtaa ttttttgtagt gatgaggtct ctctatgtgg ccagggctgg    15660
tctcgaactc ctctaccttt ctcttataag gacctttgtg attacaccgg gcctacctgg    15720
ttaatccaga ataaccccct catctcaaga ttcttaatca catacacaaa gtctgtcttt    15780
accacttaag gtcacatatt cagagcttcc agggattagg ctgtgaacaa ttttggggag    15840
cattattctg tcgcccacac tgcgggtagg ggtgggaagg tcagactgta ggggatttag    15900
ccaaacaagt gaatgtctac ctgtgaagcc gtggaggtac tgggtacaga acaggtccct    15960
gtggcgggat gaggtctgtg cctgggtcct cctgcctctc acagtgaagc ccccgtgtga    16020
ctgtgggaaa gtcacccccct ccctgggttt tactctcctc tgtaatgaca gctgtgtgtt    16080
gatataatag taacctgctt acccaatgtt ccggtgtatt ttgctcacta cattctcaca    16140
gcagccctct gaagtgtaag tactactgtt ggcccatttt ccagatgagg aaacctgaga    16200
gaaatttggc aactcacccc catttgcaca ccgtagaagt ggcagagttg ggatttgaac    16260
caaggagcct gggtcttaga gtttctgctc ttaaaggttt gacctgcctt aaaattctgc    16320
cattttaact ttttttttt ttttgaggca aagtctcgct ctgtggccca ggcgggagtg    16380
cagcagtgcg tctcgtctca ctgcaatctc cgcttcccag gttcaagcaa ttctgcctca    16440
gcctcccaag tagctggaat tacattcaag caccaccaca cctggctaat ttttatattt    16500
ttagtaaaga caagagtttt gccatgttgg ccaggctggt cttgaacttc ggacctcaag    16560
tgatccacct gcctctgtct cccaaagtgc tgggattaca ggcgtgagcc accacgcttg    16620
gccccattgt cttacctttc ttttagccct tttattttcc ctcttcatgc cctgcctgtt    16680
caccatcatc tgtgtcttct cttcactctg agtaacagtt gggtgttcag ttgaccaggc    16740
cgtagtccac gccattccta ctctccctga gctatgagtg aatctgtgac tcttgtaaat    16800
aacaggggga cacacagagg tgtttctgaa atttccacat gttaagttat cttgatttaa    16860
tcccagcact ttgagaggcc aaggcaagag gatcacttga ggccaggagt tcgagaccag    16920
cctgggcaac atggcgagac ctcatcccta caaaaaaat taaaaattag ccaggcatgg    16980
tggcatgtgc ctgtaatccc aggtacttgg gaggctgagg tgggaggatc acttgggccc    17040
aggagttgga gcctgtggtg agctatgcag gtgccactgt actccagcct gtgcaataga    17100
gtgagattcc ttctcaaaaa cagaaattta tcttgggcac caggcagaga tgtccagcct    17160
gtatcatctc tgagcttagt ggcctcagtt ttcccaccag gccaatttct gatgggattc    17220
tgctcggaag cccccgcgtc ctgttcagct gctcaaggga agttctcagc cttgacact    17280
atccgtccta ctcgtccttc cctttttgggc tctgtctgcc tgttggccat tcaccagag    17340
```

```
agggatgggg tcagggagga gaaaggccct gagactcctt tgacagtggt gtcaggctga    17400
acacagtggc tcatgcctgt aattccagca ctttgggagg ctgaagcggg tggatcactt    17460
gaggtcagga gttggagacc aggttggcca atatggtgaa accctgtccc tcctaaaaat    17520
acaaaaatta gctgggcttg gtggcgcatg cctgtagtcc cagctactca ggaagctgac    17580
gtgagagaat cgcttgaacc cgggaggtgg aggttgcagt gagccgaggt cgtggcactg    17640
cattccagcc tgggcaacag aatgagactc tatctcaaaa aaaaaaaaaa caaaaaaaaa    17700
caagggtgta ccttcagtgt cacaagcaag cactgaaggt ggagcactta cacggtagca    17760
actcgatgtc cccttctctc tccacacctg ttggctggaa ctgttgacgt tgtgacatct    17820
ttgggtacca gcaagttaga gactcagaat ctgcttgata cccatgaaga aagccagtgt    17880
catttctggg gaacggatga caccttgtcc ccattgaaca agtggcttta gggctacccc    17940
aaggaccagg tgatgagcgt ggagtgacaa gtatttctga atttgatggg gtggggacat    18000
tggggagcct gctcatgact caaggttctg aatggataat acagtggtaa gaactaccct    18060 ctctctttc ttttttttt tttttcgaga cagggtcttg ctctgttgcc caggctggag    18120
tgcagtagtg caaacatggc tcactgcaac cgctgcctcc caggctcagg tgatcctccc    18180
cactgagctt cttaagtagc ttggactgca ggtgcatacc accactcctg gctaattttt    18240
gtcttttttg tagagatggg gtctcattgt gttgcccagg ctggtctcga actcctgggc    18300
tcatgccatc ctcccgcctt gggcttccaa agtgctggga ttacaggtgt gagtcactgt    18360
gccctgctgg aactaccgtc tttatttttt gagacagagt ctcgctctgt tgcccaggct    18420
ggagcacagt ggcatgatct cagctcactg caacctccgc ctcctgggtt gaagcacttc    18480
tcctgcctca gtcacccaca tagctgggat tacagggctg cgtcaccacg cctggctaat    18540
ttttgtgtat ttattagagc cgggtttcac catgttggct aggctggtct tgaactcctg    18600
acctccagtg atccgcccac ctcggcctcc caaaatgctg ggattacagg cgtgagccac    18660
catgcccggc ctgaactac cctcttgaca tctttccata gctggaatca gaactggaat    18720
ggatgctggc ccaaacaagg ggtctcctcc gctgagtgat gattttagca gtgccataaa    18780
cttccaccaa ggagaaaaaa atgaaccaac cagtcttgag gtttggagac tgcggcagct    18840 tttcttctg acttcatttt gtccatgtgt acactcccc acacttccct ttcaacctct    18900
gtccacccat gttttttgttg ttgttttgtt ttgttttgtg tttttttttt tttccagacg    18960
gagtcttgct ctgttgccca ggctggagtg cagtggcacg atctcagctc actgcaatct    19020
ccatctcctg ggctcaagca attctcctgc ctcagcctcc cgagtagcta ggattacagg    19080
cgtgtgccac cacgcctggc taattttttgt acttttagta gagacgaggt tttgccatgt    19140
tggccaggct ggtctcaaac tcctgacctc aggtaatccg cctgcctcgg cctcccaaag    19200
tgctgggatt acaggcgtga gccactgcgc ccagcctgtc cacccatgtt ttatcccgac    19260
ttgatctcct cctgcctgga catcctaggg tgccctgttg agaaacaata cactgccccc    19320
aggaatcccg gaggaaatga aggactccag gctcaattca cggattccag ttcttgagca    19380
tatttggtga tgtgctggca tctgcaccat aaatcctcgt gttaccttga gctgaactgt    19440
gagaccatct atatggaggc ttgtcattac ataaacatct tcctttacaa atgtcgtttt    19500
ctcagattct atgttagagc tattggagta agcccttcct gctgtttcat gtctactcct    19560
aaatcttttt ttttttttaa cccaaggtag agtcttcctc tgtccatgcg cccccctacc    19620
cctgcccagg ctgaattgca gtggcactat tatagcttac tgcagcctca acctcctggg    19680
```

```
ctcaagtgat cgagggatcc tcctatctca gcctccgagt agctgggact atagacatgt   19740
gccatcacgc ccagctgatt tgtttgattg ttagtagaga tggcatctca ctatgttgcc   19800
cgggccggtc tcgaacttct aggctcaagc gatccttctg ccttggcctc ccaaagtgtt   19860
gggatttcag gcatgagcca ccacgtctgg cctgctccca aatcttcatg cctttccaga   19920
tggatcttgg tgtcctgttt tcatacctag gtattgcttt ctacaaactg ttgaagtacc   19980
agagtgacca acttgtccca gtttgcctga gactttccta gatttagcac caaaagtcct   20040
gcatccaggg aaaaacccct ctgtccaagg gagactggga cattgggtca ccctatgaag   20100
cacccataat gttttggccc tcttttctagg tgctgggatg cagatttag tgtcagttcc    20160 tgctcttatg gggtctatga ccagatagga agacagacaa gtgaagaaaa ctgctttatg   20220
acaaatacag caaacaaaca tgagttaata acagctgaca cataccgagt gcttatgtgt   20280
tccaagttgc tctggtcctt ttttgcaaat ggattcattt catcctctca agagccttat   20340
gaggaagaaa ctatcagtgt acccatttta cggatgggaa aactgaggca ctaaagtcat   20400
gccctggggc atggggcgcc tggaggaacc caggggtct agctccagag tctgtgccct    20460
tgacctctgc accatataga gaggctccag gaggaatgaa ttctcccggg ggcaagcaga   20520
gagggcttct tggaggaggt gacacgcaag ctaagcggaa tttgccagac ccatcaggaa   20580
ggaggcagac ggaagaaaga gcatgcccgt gacatgtttg ggaacatcca agcaaggcag   20640
gtgtggcggg agacgccacg agagactgtg cggttggtag gggcaccagt gcatcctggg   20700
aatcttctca gtccccacaa acccggagca gggagtcgcg ctagtcaaga gcacaatgag   20760
gggtgtcaga aagacccacg tggcttgatt ttaaacaaac gggcccggga tggactgaac   20820
caagaccagc agccaactta gaggctcagt tttaaggcct tgacttggga tagtaagatt   20880
agagatttcc agcagtgtct cctccccgca cctccccccca cccccccgcc cccgctttt    20940 tagtgaagag aaagtcacat aaagataacc atttaaaagt gagtaattca aggccaggcg   21000
cggtggccca tgcctgtaat cccagcactt tgggcggctg aggcaggtgg atcacttgag   21060
gttaggagtt cgagcccagc ctggtcaaca tggtgaaacc ccgtctctac taaaaatata   21120
aaaattagcc gggtgtggtg gcaggcacct gtaatcccag ctattaggga ggctgaggca   21180
ggagaattgc ttgagcctgg gaggcagagg ttgcagcgag ccaagattgt gccactgtac   21240
tccagcctga cgacggagc gagaatctgt ctcaaaaaaa aaaaaagat aattcagtgg     21300 catttagtaa gttctgtact ccagcctgag cgacagagca agactctatc tcaaaaaaaa   21360 aaaaaagat aattcagtgc atttagtaag ttcgtagcat tgtgcaacca tcaacttcca    21420
tctggttcca gaacattttc atcatcccca aaagaacccc atacccatt cctcccactg     21480 ctgtacaccc atccctggcc accagtgatg tgctttgtat ctctatgaat tcacctattc   21540
tgggcatttc atctcagtgg aatcatttga tctgtagcct tttgtgcttt cgaggttcat   21600
tccagggctg tcgtggagcc ggaatgatca gtgataaaac tgctaggctg gccaccccgg   21660
gcttcccgaa gtctgatctt ttcctttgca tttaggattc aaggtcatac ttagttagca   21720
ggagcgatac cataatcatg aacgtggttt tcccagggtg aggcttatcc ttgcactccc   21780
ctgcaatctc cccattaaaa aaaaaaaatt caagattcta tctagaacac tgtacctttt   21840
gacctgcagg tttgattgtg caaacgttga atgaacccgt tttgggcgcg caaggagtag   21900
gatgacaccc aggaccttgt gagtgcccga agtagcagct tgcactggcc tattccagag   21960
aattctgagg ctgttgaggc tgaattgttt agaagcagat ctgttgctga aagtgaggtc   22020
cctcgtggag tttatttcca cgtcccgagg attccagatc ggtgcattaa tatcagttaa   22080
```

```
gggcacggat gatcgctggg tctgacactg tggcttctcc ctgcgggttc ctgggttttt   22140
tgcctccact tttaacaaaa ctgaggccgg gcgcggtggc tcacacctgt aaccatagca   22200
ttttgggagg ctgaggtgag tggatcactt gaggtcagga gttcgagagc agcctggcca   22260
acatggtgaa acccctgtct ctagtaaaaa tacaaaaaaa ttagctgggt ttagtggcac   22320
gtgcctgtaa tcccagcttc tcgggaggct gaggcaggac aatcgtttga acctgggagg   22380
cagaggttgc agtgagctga aatcatgcca ctacactcca gcctgggtaa cagagtgaga   22440
ctctgtctca aacaaaaaca caagcaaaac tgagatggag atgctgtctg ggttgacaag   22500 cacgccccccc accccaaccc tttgtctttt gctaagggct tgaagcagta aatatgcagc   22560
tttgggcacc ctgcctccag ggaaattctg agctctctca gaatttcatt gttttcttc   22620 tcaatatgag agggctgagc tttgtgactt tccatcctcg gctgatcatt aacgttctat   22680
tgcctgttta ctaagaagca ggtcaccttg aattgcaagg tgcccagtga cagaatgagt   22740
tggaacccat cattggcagg tatttttgc atggcatcaa gtatgtggca taaaagtgca   22800
cagtaaacgc actttcatgt attagggagg cagaaagaga ggtgatccct ccagagttca   22860
aatgtgttgc ttccactgag ggtgtatttt cctttcatga ttttctggt ttaataat    22920 ttctggccag gcgtggtgac tcacgcctgt aatcccagca ctctgggagg ccaaggcggg   22980
ctgatcatct gaggttggga gtttgagacc agcctggcca acatggtgaa accctgtctc   23040
tactaaaaaa tacaaaaatt agctgggcgt gttggcaggc acctgtcatc ccagctactc   23100
gggaggctga ggcacgagaa ttgcttgagc ctgggaagcg gaggttgcca tgagccaaga   23160
tcacgccact gcgttccagt ctaggcgaca gagtgagact ctgactcaaa aaaaaaatt   23220 attattatta taatttttt gtgtagagat atggtctcac tctgtcaccc aggctggagt   23280
gcagtggtgt gatcacagct cactgtaacc tcaagctccc aggctcgagc aaatcctccg   23340
acctcagctt ccttaatagc tgggactaca agtttgtgca accgtgtctg gctaatatat   23400 atttttttaat taaaaaaaat ttttaaagat tgtctttata tatgattttg tgactctatt   23460
tttttttctt ttgtttttgag acaaggtctt gctctgtcac ccaggctgga gagcagtggc   23520
gtgatcctag cttattgcag tctcaaactc ttgggctcaa gtgatcctcc taccttagcc   23580
tccagagcag ccaggaccac aggcatctgc cataacgccc ggctaatttt tgtaccattt   23640
gtagagacat ggtctgaatt tgtttcccag actggtctca aactcttggg ctcaagtgat   23700
ctgcccacgt cggcctccca aagtgctggg attacagacg tgatccaaca tgcctgggca   23760
agaatacctt tcgttgagca aattgttgag aggtagaatg aggaaaactt ttggctaaaa   23820
gggaccccaa gatatcccaa gtggcatatt tatagatgtg aaagtgattc cacagctggg   23880
catgtcagat caaaattctc catggatcag gaatgcctcc ttttcctttt ctgtcaccac   23940
cggtcacatt tggctactta atttctgggc tccagtgcag catggaaacg cgaggccctt   24000
tgttcaaaaa gtgttcgaat ttcttttctt ccttctttt tttttttttt ttttttttt   24060 gagacggagt ctcgctcagt cacccaggct ggagtgcagt gacacgatct cggctcactg   24120
cagcctccat ctcccaggtt cacagtgtgg agaggcaggg cacggtggct catgcctgta   24180
atcccagcac tttgagaggc tgaggcagga ggatcacttg agcccaggag tttatgacca   24240
tcctgggcag cttagcaaga ccctgtctct aagtaaaatt aaaaagttat agccaggtat   24300
ggtgacacac acctgtagtc ccacctactc cagaggctga gacaggagga ttgtttgagt   24360
ctacgagttt caggctgtgg cgagctatga tcatgccact gtactccagc ctgggcaata   24420
```

-continued

```
gagtgagacc ctgtttctct cttctttct cccttccct cttttttaaa aaaaagacat   24480
tgtggagagt gtgtgtgtga gtttagggtg aggggggacta attgctgttc taagagtttc   24540
gtagttgggg gggtgataag gaggggatgg ggggtgatga ggagagggat ggttggtggg   24600
tgggcctctt atcccaggag ataagccaaa ttgaaatgaa ggcgcaaaac aagggaaaca   24660
aaatgggact aaccgtggtg gcatttcctg gccttgggc ctgagggagg gaagactgtg   24720
gaatttattt agaaaacttc caaaccagcg gttatgagtc ttttttacta ttctggcctg   24780
ttgctcttgt tctttcaga attataaatg tgtttgtgtg gctgtttgat ctcaaagcaa   24840
tgctcagaag atgcagtgtc tcgaaatccc agaagataag atgttaccac atgaaagatg   24900
gtctcaataa aggggagag gcggtggccg aggccttaat ttccaaaacg agaaactggg   24960
gcccacccat cttttaaagg tcgtcaaaag aaagctccca tcctcccatc ccccacacct   25020
gtgtgttgac tctgtaaaga tgcagtttcc tcactttggg aggagaggcc gtggttttttg   25080 caggaattgc gccgctgccg aattcagcca ttgcctcttg gaggtttagg atgccccagg   25140
ccttgttttc cctcaaagca ttccattggc aatcacgacc aaccatgctc cttgaggatt   25200
tctgtacaca ctggcttttc ctggtcttgt aagttttat acgagtcagt tttcaccata   25260
aatcatggag gtgggtctgg ggctgtgacg gcgagtcctc gacgttcaac ccggatgtag   25320
gtcactccag accccaggg tgccctgtcg ttccctttgc tggaagtttc aacaaagcca   25380
gaagcagatg tcaggggttc ccgggggtcat ctggagggga tgtccgctga gtttaggggc   25440
aagctgggac tgctgcattt ctgttcctgt acgtcagagg aaactagcaa cacgcctcaa   25500
accactttac accatgtctc agtgttaaac cagagcctgt tttcacaaac acctcctgcg   25560
atctcattac agccccaccc tgccctcctg cttctgtggc cttctctact ttgcttcttg   25620
ctcctcttaa agaccttctg tctcatctgt cttttctggg gttgggcctt tccccttctc   25680
tataaccttc tgtgactccc acggctcaca gctttgctgt atattaggag cagaaagcaa   25740
gcttcattac atcatttaaa attttttagt agctacattt tttttttttt tgagatggaa   25800
tctcgctctg tggcccaggc tggagtgcag tggtgtgatc tcagctcgct gcaacctctg   25860
cctcccaggt taagtgctgg gattacaggc gcacgccacc agacctggct aatttctgta   25920 ttttagtag agatggggtt tcaccatgtt ggccaggctg gtctcgaact ccttacctca   25980
aatgatccac ccatctcagc ctcccaaagt gctgggatta caggcatgag ccaccgtgcc   26040
tggccgccac atttaatgta tttatttatt gattttgag acagagtctc actctgttgc   26100
ccaggctaga gtgcaatggc gcaatctcag ctccctgcaa cctccacctc ccgtgttcaa   26160
gtgattatcc tgcctcagcc tcctgagtag ctggattac aggcgcccaa tatcacacct   26220 ggctaattt tgtatttta gtagagacgg ggtttcacca tgttggccag gctggtctca   26280
aactcctgac ctcaggcgat ccgtctgcct tggcctccca aagtactggg attatagtcg   26340
tgagccactg tgtctggcct cttttttatt tattttgttt ttatttattt attttgaga   26400 cagtctcgcc caggctggag tgcagtggcg cagtcacggc tcacttgaac tcctgggttt   26460
aagtgattct cccacctcag cctcccaagt agctgggacc acaggggtgc accaccatgt   26520
ctggctaatt tttaatttt ttgtagagac agtgtctccc tatgttgctc aggctgatct   26580
agaatgcctg ggctcaagcc atcctcctgc ctcagcctcc caaagtgctg ggatgacagg   26640
tgtaagccac catgcccggc ctagtagcca catttgaaa ggtacaaaga aacaggtgaa   26700
attaacaata cattttactt aacttcatat atctaagctg tggtcatttt aatatatcaa   26760
tataagaaat tattaatgag atattttaca ttcattttt cctactaagt tttgaaaccc   26820
```

```
agggtgtatt tttacattga cattctatcc caaattgaat gctaaatttt tatcaaaaaa    26880
cattttgatc tatattcagt gttcatcaaa tttaccattg aaaaaatgat tcatatattc    26940
aagttgtccc agacttacat aaaagcttcc caataattga attgttagtt ttcacattta    27000
aattgcttaa acttaaatac aagtaaaaat tcattggcaa gtaaaagat gaaaagaag     27060 ctaaaacaaa aaaaattcag ttcttcactc acactagctc atttcttttt ttcttttaga    27120
catagagtgt cgctctgtca cccaggctag agtgcagtgg catgatcatg gctcactgta    27180
gcctccacct gctaggctca agtgatcctc ctacctcagc ctcctgggta gctgggacca    27240
gaagtgtgca acaccatgcc tggctaattt ttttaatttt taaaattttg tagagagagg    27300
gtatcactat gttgtctagg ctggtcttga actcctgggc tcaagtaatc ccactgcctc    27360
gacctcccaa agtgctggga ttgcagtcat gagcccccgt gcccggccac aagccacatt    27420
ttagacgccc aataacctta cgtgactggt ggctgctata ttgggcagca gatacagagc    27480
atttccatcc tcacagaaga ttctgttgga cagcactctg atagaaagaa gtcttgaaca    27540
cgtgttctcc aagggacttt caaagttttc tagaatgcag ccccaaccta tctttactta    27600 ctgacttct ttttatcacg ttcactcccc cgcctctatt ccactttgtt tcgtttgttt    27660
gtttttgaga cagagtctcg ctctgtttcc caggctggag tgcagtggag tgatcatggc    27720
tcactgcagc ctcaacctcc taggattaag caatcctcct gcctcagcct cctaagtagc    27780
tgggattaca ggtgtgtgcc actacacctg gctacttttt ttattcgttg tagagacagg    27840
gtctcactat gttgcccagg ctggtggtga attcctgggc tcaagtgatc ctcctgcctc    27900
aacctcccaa agtactggga ttacaggcat gagccactgc acccagccct tttgttttgt    27960
tttgttttag atgggggt ctcaccatgt tgcccaggtt agtcttgaga tcctgggctc    28020
aggctatcct gccacctcgg ctccacagag tgctgggatt acaggtgagc caccgcacct    28080
ggtctctgtt tccactttga ggtgaatacc ctttcttcgg ttcctccaga gaagtctcct    28140 cttggggct tggtttagag gcagggcttc tgagaaggac tctacccttc tccctgcagt    28200
gggattaatt gctgccttgg cttcccacga gttctagaaa atgaggcaga cagtgtcggg    28260 agagggagt ggtggttgtg gctcgctgcc ccggagcctc atttcccatt tctcccgaga    28320
caggtttgaa tggctcttct aaggcagcct gaaccctgcc cagttagaaa acagccaca    28380 caaagaacag cactgtgtct gcttccagct gcccatggc tgctggatca tggaacatca    28440
gacaggagca cactctgggt gcagggtgta attctaggcg agcagcagct ctgccagggc    28500
tggagggaaa tcctttcttt gccctcacaa aagaaaatgt gtgcctggct gctctggtgc    28560 tcattttca aaatgagaac tggagtctat gtgtatttcc ttcttaaaaa gctataacac    28620
agaggctggg cgcggtggct catgccttta atcccagcac attgggaagc caaggcggga    28680
ggttcacttg cccccaggag tacaagacca gcctagatag caaagtgaga cccccatctc    28740
tacaaaaaat gaaaacatta gccgggcggg ggggcacatg cctgtagtcc cagctacctg    28800
ggaggctgag gcaggaagat cacctgagcc tgggtggtgg aggctgcagt gagctgagat    28860
cacaccactg cactgtagcc tgggtgacag atcttgtctc aaaaaaataa aacaaaacaa    28920 aaacaaaac tataacacac atacaaaaaa gtatatacat tttaattgta caactgagat    28980
ttttacagac tgaacatacc tctgtaacca gccccaggt gaagaaagag aacaggaccc    29040
gccccccgca aaggccccct catacccctt tccagattct tcttcctctt ccaagagtaa    29100
ccgctccatg gattcatttt gcctatttct gacctttatt taaatagcat catacagtgt    29160
```

```
gcattttgtg gcatctggcc cctttgctat ttgtgataat ttgtggttgg tttttgaatg   29220
cctttatctt ttccgttacc tgaaacagtt agtgaaaacc acagtggttt aaaaaccaaa   29280
aaaaccacaa aaaaacaaac aaaaaaaaac aacgaagaag aaacaccaga tatggaaggt   29340
acgtaggtca ttgtctggta atggtttaag atgtgaagaa gaaatgaccc ttatttggtt   29400
gatgtttcca ctttggattt tccaggtttt ggtgattttg ggtagtaatt atttacttttt  29460 tgattaattc tggggtcttg aagggacatt aaccctcttc ctagcttttg gacaaagctg   29520
gatggaagtc attttctcag aatttctgtt tgccagaaag aaaattgaag acttaggtga   29580
aaaagagagg gagagatcaa ctgaatttct tatctggtat gttctgtttc tgttttaggt   29640
aaaatgtcgg ttccaggacc ttaccaggcg gccactgggc cttcctcagc accatccgca   29700
cctccatcct atgaagagac agtggctgtt aacagttatt accccacacc tccagctccc   29760
atgcctgggc caactacggg gcttgtgacg gggcctgatg ggaagggcat gaatcctcct   29820
tcgtattata cccagccagc gcccatcccc aataacaatc caagtacgtg tggcctccca   29880 ggccccccctt accattcctt ggccctccac cctgggaatc aggagagtga ccgaagtgac   29940
tctgccaaag agtctaagtg aagtgccagt acgttccagt tttaccccct taccttgaaa   30000
ttccacacgc agtcttttag attccatgtt ggtgaggctc acagcttttc cgtaataaag   30060
tatggtttag gatctttccc atggtcatca tatacgaatc ttttggcaca tctcttggag   30120
gcacaaccaa ctttcttctg agaatgggag tttgtgtctt aagggcccgc acacttcctc   30180
ctgaggtctg atgcagaact ctgccctga ggccagggcc gaggtaggaa taggaggag    30240 aagaaaccgt cctgagcaat gtgtgattgt gttttcatac cagctcaccc tcaatgcaag   30300
ttgctcttct gcttttgagc aactagatgg tccctgtcct ttggtgcttc cttccgccca   30360
agggtgccct ggtatgtcac tgctttagta tcacaggtag ttctgaaaga aatctttagc   30420
tcagagaggg ggcccgtgaa tcagactgcc tgggttcaca taacctcctt gtgcctcagc   30480
ttccccattt gtaaaatagg tttcatcaag tacctattta taaatatcag tgagttgtta   30540
acatgagagg aagttgtgtg tgccaaatac agagtactcg tttgataaaa gtgaactctt   30600
attgttgtgt tcaagttatt ttgagctgga agaggatgag ataatgactt tagattctta   30660
gaccatcctg tgatcaataa atagtttctt tttctttttc tttttttttt tttttgagac   30720
agggtctcac catgttgccc aggttggagt gcagtggtgc agtcatggct cgctatagcc   30780
tggacctcct gggctcaagt gatcctccca cttcagtctc tggaatagct gagactacag   30840
gcatacagca ccacacctgg ctaattttta aattttttgtg taaatcgggt ctcactgttt   30900
ttccaggctg atctttaact cctgagctca aacgatcttc ccacctccct tggcctccca   30960
aagtgttaga attatcagca tgagtcacag agcctggtcc aaataactta ttcttgaacc   31020
ccaaaaacac ttaataaaat gtatgaacag ggtgtggtgg cttgcgcctg taatcctagc   31080
tactgaggag gctgaggcag gaggatcacc tgaggccagg agttccaaac cagcctgagt   31140
gacatagtga gacattgtct ctatgaaaat aaaattagct gagtgtgatg gcttgtacct   31200
gtagtcccag ctacttggga ggctgaggtg ggaggattgc ttaagcccag gaggttgagg   31260
ctgcagtgag ctatgattgt accctgcac tccagcctgg gcaacacaac aagaccttgt    31320 ccccctgcc aaaaaaaaat tacacgtaag tgctaaagta tgatttaata ctacttttct   31380
ggaaggaggg tctttctatg agtattacta agttcagtta actctaggca gtaatttccc   31440
cctaattcat ttgttatata aatgacattc taacgtaaaa aggaacagaa ggaagttgct   31500
ttaacaaaaa tatgagctta acaactgaag tgcttgatga ttttcatcac cctgggttct   31560
```

```
ctctttttttt ttttttttttt tttttttgagg tagagtcttg ttctgttgcc caggctggag    31620
tgcagtggca taatctcggc tcactgcaac ctctgcctcc caagttcaag caattctcct    31680
gcctcagcct cccaagtagc tgggactaca ggcacgtgcc atcatgcccg gctaattttt    31740
gtctttagaa acagggtttc accatgttgg ccaggctggt cttgaactcc tgacctctgg    31800
tgatccacgc acctcggcct cccaaagcca agggatttgc tgggattaca ggtgtgagcc    31860
accgtgcccg gcctggattc tcttctgatt cttgagaatg ttcgaacatg ttttcacata    31920 gcttttctt cctagcatta ttttatattt tcatttcttg tatcaacaca gttcactagc    31980
ttgttgtctt acagagttgg cctgcgtttc ctggcttggt aaactctacc cttatcattg    32040
gctgtcagag tttatcaaag ggtttgtgta aagagagtgg attatttatc aagagctgct    32100
aggcacagtg tgaggctggt taaaatttat ttatttgttt ttgggactga gcgtcgctct    32160
gttgtccagg ctggagagca gtggcgcaat catgattcac tgcatcctca atctctcaga    32220
ctcaactgat cctcccacct cagcctcctg agtagctggg actacaggcg tgtactccca    32280
cgctgggcta attttatat ttttttgtag agatgaggtc ttgtcatgtt gcctaggctg    32340
atctcaaact cctaggctca agcagtcctc ccacctcggc ctcccaaagt gttgggatta    32400
caggcatgag ctaccgcgcc cggtcctcct ttctttttga ggctgaatca tattctggtg    32460
gatggataaa cttcgctgtg ttagtttatt ggtccgtcga tggacactgg tgttccttcc    32520
ccttttggct ctcatagata gccagacgat gaacgcatgc tatgaacaca aatgtacaaa    32580
tataatattt gctggcatcc ctgcgttcct ctctttgtcc tgtagtgaat gctattggcc    32640
ttgtttcctg agcaacctgt gtttgtccct ctccctttca tcagttaccg tgcagacggt    32700
ctacgtgcag caccccatca ccttttggaa ccgccctatc caaatgtgtt gtccttcctg    32760
caacaagatg atcgtgagtc agctgtccta taacgccggt gctctgacct ggctgtcctg    32820
cgggagcctg tgcctgctgg ggtgagtctg cctcccactt ggcccaagc catcctgccc    32880 ttctctctgg gtgctggcgg gggtgggttc tcaactgcac catgcttgac attcagggcc    32940
agacatttgt gttgtttttt tttgagatgg aatctggttc tgtcgcccag gctggagtac    33000
agtggggcga tctcggctca ctgtaacccc cactgctcag gttcaaacga ttctcctgcc    33060
ttagcgtccc gtgtagctgg gattataggg gtgcacaacc acgcccagct tattttagt    33120 agagctggca tttcaccatc ttggccaggc tggtctcaaa ctcctgacct caggtgatct    33180
gcccaccttg gcctcccaaa ctgctggggt tacaggtgtg agccactgtg cctggcctaa    33240
ggcatttctt tcttttttg tgatggattc tcactctgtt gcccaggctg gagtgcagta    33300
gcacgatccc ggctcactgc aacctccgcc tcccaggttc aagctattct cctgcctcag    33360
cctcctgagt agctgggatt acaggtgtgc accgtcaggc ccggctaata ttttgtactt    33420
ttagtagaga tagggtctca ccatgttggc caggctggtc tcgaactcct gacctcaggt    33480
ggtccacccg cctcagcctc ccaaagtgct gggattacag gtgtgggcca tcatgcctgg    33540
cccaagacat ttcttattg taggggtgt cctgtgcatt gtaggatatt gaatagcatc    33600
cctggccccc acccgcttaa tgctaggagc accacgctcc ccagtgttct gaacaaaaat    33660 gcccctggg aggccaagtc atccctgctg ctcttaagcg tatccgtccc cagaaattgg    33720
tcttccgtct tttcttcttg cttatctgct gaaaccacgc cctgcatgta gggacaagct    33780
tcacagctgc ttccagctgt gtacagggca atatcctcag ggattccttt ttcttctaga    33840
atttcatgac ctaaataata atgttttgct cgagcccgag ggaagcttta aagaatctgt    33900
```

```
acattaaaat tcttcatagg aattgcttca aaacttctta tccttttatg acccgaagta    33960
tttttcccat tgcccatgca gggaaattat ataaattttta tgtctgcacc aaaggtatta   34020
tgtttaaaga gataacagtt tctgttctgg gagaaaaatc tgaggaaaca caatcaattt    34080
tttgtttccc accaagcagg taaaagtagc ttccttatac ctggccacgt gagccactca    34140
gaaaacccca aggggctcca ttcttttcct tgaaggaaac ggtgtttgtg agtttcagga    34200
gcctcatgca accggcacgt tcctccacat tgtcctttgg tgacttgagg ttgagaagga    34260
acaatatttc tcttcctaac ttcaataaga ggctcagagt cccagagagt ttagttaact    34320
tccttgaggt catgtgttaa ataaggaagg aaggagacaa aacagctttc tgggcacctg    34380
attccccctc ttgcccacag gactctgctg ttgttttcat tctgtgggca gaaaatgctt    34440
aaaaaaaaaa aaagtccatt gcctctggat atttgtatta aaacaaattt tttatctttg    34500
gaatcaggga aagatggaat agaaacttgt tttgttttgt ttgaggctga gtcttgctct    34560
gttgtccagg caggagtgca gtggtacgat cgtagctctc cgcagctttg atctcctggg    34620
ctcctgcaat ccgcccagct cagcctcctg agtacctggg accacaggtg tgtgccacca    34680
tacctagcta attttttaaat ttttttttttg tgtgtgtgga agcaggggtt ttactatgtt   34740
gcccaggctg gtcttgaact cctggactca agcagtcctt ctgccttgac ctcccaaagt    34800
gctgggatta tagaggaata gaaacttaca ttgagtattg gcctctgcca gtctggcttt    34860
agaaattgag gcaacctttc tttccctccc tttgttcctt ccttaaacat ggtagagtgg    34920
gttcaaatcc tgcctctcac tagctgtgtg gccatgggca agtgacttta cctctctgtg    34980
cttcagtttc cccatctgta gacggggtg cggggcaata acgcccacct cagggcctgc    35040
tgaggatgaa atatgtgtgt gtgctgcctg gagccgtgcc tgcacctgta agccataggt    35100
taggattcct gctgaatgga ttgactgccc ttatttgagc tctggaaagc ttaggcaata    35160
ggaggaaatt tctttcatga gataatttcc tcatcagaat atttccaaat tctgctttat    35220
gtaaaccagc gtcttcctgt gaagggttga gttttaactc cattttttggc aaacattggt    35280 tgtcaggcgg tctgaggttc ctgcctgtgt gtgccaaagg tggattatgt aggttaagag    35340
gcattatttg gggaactcta cttggttgct gtaagaagca gcctgtctat atggaaaaga    35400
gatcagtaag acgggggttg gcaaaacgac cctggagcca ggcgcctgtt ttaagtttta    35460
cgggaacaca gccacgcctg ttggtttttg gattctctgt ggctgtcttc tcattccaag    35520
ggcagagttg agcagttgca acagagacgc catggctcat caggatgaaa gtatgtggcc    35580
gggtgtgtgg tggcttccac ctgtaatccc agcaatttgg gaggcggagg tggaaggatc    35640
acttgaggcc agcagttcaa gaccagcctg tgcaacatag caagacccca tctctacaaa    35700
aacaaacaaa acacagcaac aaaaagacta aaagatctac tatctgtccc tttgcaaaaa    35760
aagttcacca agcccatcta agactttgaa agactcccaa atgaccccag atttgaaaat    35820
aatactcaaa ggggctctgt ctgtaggagg agccttggca ttggctggca tgttaatttc    35880 ctagggtgt catcacaaat tacaacacac ctagtgttta aaacaacaga tattaactct    35940
cacaattcta gaggccagaa gtgcaaaatc aaaatgtcag caggggccgg gtgtggtggc    36000
tctcgcctgt aatcccagca cttggggagg ccaaggcggg tggatcactt gaggtcagga    36060
gtttgagacc agcctggcca acacggtgaa accccaactc tcctaataat aaaaaaatta    36120
gctgggcctg gtggcatgcg cctgcaatcc cagctactca ggaggctgag gcaggagaat    36180
tgcttgaacc caggaggagg gagaattgct tgaaccctgg gcgacagagc gagactccat    36240
ctcaaaaaca aaacaaaaca aaaccaaaaa ctaaaatgtc agcagggcca cgctccctcc    36300
```

-continued

```
taaggcttca gggagaatca ttttttgcct cctccagctt ctagtaggtc caggtgtcct    36360
tggcttatgg cctcatcact ccagcttctg cctctgtctt cacatttcct tctgccctct    36420
ctgtatctct gtgtgtcctc tcctcttctt ctaaggtcat tgggttttag gggtccgcct    36480
ggataatcca agatgatccc atctcaaaat tcctaattat actggcaaag acccttttta    36540
caaagaagga catgaacatg gttttggcag ccagtgttca ccctgttgtg atcagtaacg    36600
cgctccgtgt gtctctctct cctcccaggt gcatagcggg ctgctgcttc atccccttct    36660
gcgtggatgc cctgcaggac gtggaccatt actgtcccaa ctgcagagct ctcctgggca    36720
cctacaagcg tttgtaggac tcagccgac gtggagggag ccgggtgccg caggaagtcc    36780
tttccacctc tcatccagct tcacgcctgg tgaggttct gccctggtgg tctcacctct    36840 ccaggggggcc cacctttcatg tcttcttttg gggggaatac gtcgcaaaac taacaaatct    36900 ccaaaccccca gaaattgctg cttggagtcg tgcataggac ttgcaaagac attccccttg    36960
agtgtcagtt ccacggtttc ctgcctccct gagaccctga gtcctgccat ctaactgtga    37020
tcattgccct atccgaatat cttcctgtga tctgccatca gtggctcttt tttcctgctt    37080
ccatgggcct ttctggtggc agtctcaaac tgagaagcca cagttgcctt attttttgagg    37140 ctgttctgcc cagagctcgg ctgaaccagc ctttagtgcc taccattatc ttatccgtct    37200
cttcccgtcc ctgatgacaa agatcttgcc ttacagactt tacaggcttg gctttgagat    37260
tctgtaactg cagacttcat tagcacacag attcacttta atttcttaat tttttttta    37320 aatacaagga gggggctatt aacacccagt acagacatat ccacaaggtc gtaaatgcat    37380
gctagaaaaa tagggctgga tcttatcact gccctgtctc ccttgtttc tctgtgccag    37440 atcttcagtg ccccttttcca tacagggatt ttttctcat agagtaatta tatgaacagt    37500
ttttatgacc tcctttttggt ctgaaatact tttgaacaga atttcttttt tttaaaaaaa    37560
aacagagatg gggtcttact atgttgccca ggctggtgtc gaactcctgg gctcaagcga    37620
tccttctgcc ttggcctccc gaagtgctgg gattgcaggc ataagctacc atgctgggcc    37680
tgaacataat ttcaagagga ggatttataa aaccattttc tgtaatcaaa tgattggtgt    37740
cattttccca tttgccaatg tagtctcact taaaa    37775
```

<210> SEQ ID NO 4
<211> LENGTH: 157
<212> TYPE: DNA
<213> ORGANISM: Homo sapiens

<400> SEQUENCE: 4

```
ttaccgtgca gacggtctac gtgcagcacc ccatcacctt tttggaccgc cctatccaaa    60
tgtgttgtcc ttcctgcaac aagatgatcg tgagtcagct gtcctataac gccggtgctc    120
tgacctggct gtcctgcggg agcctgtgcc tgctggg                             157
```

<210> SEQ ID NO 5
<211> LENGTH: 53
<212> TYPE: PRT
<213> ORGANISM: Homo sapiens

<400> SEQUENCE: 5

```
Ile Thr Val Gln Thr Val Tyr Val Gln His Pro Ile Thr Phe Leu Asp
1               5                   10                  15

Arg Pro Ile Gln Met Cys Cys Pro Ser Cys Asn Lys Met Ile Val Ser
            20                  25                  30
```

Gln Leu Ser Tyr Asn Ala Gly Ala Leu Thr Trp Leu Ser Cys Gly Ser
          35                  40                  45

Leu Cys Leu Leu Gly
    50

<210> SEQ ID NO 6
<211> LENGTH: 21
<212> TYPE: DNA
<213> ORGANISM: Homo sapiens

<400> SEQUENCE: 6
gccggtgctc tgacctggct g                                                21

<210> SEQ ID NO 7
<211> LENGTH: 7
<212> TYPE: PRT
<213> ORGANISM: Homo sapiens

<400> SEQUENCE: 7

Ala Gly Ala Leu Thr Trp Leu
1               5

<210> SEQ ID NO 8
<211> LENGTH: 21
<212> TYPE: DNA
<213> ORGANISM: Homo sapiens

<400> SEQUENCE: 8
gccagtgctc tgacctggct g                                                21

<210> SEQ ID NO 9
<211> LENGTH: 7
<212> TYPE: PRT
<213> ORGANISM: Homo sapiens

<400> SEQUENCE: 9

Ala Ser Ala Leu Thr Trp Leu
1               5

<210> SEQ ID NO 10
<211> LENGTH: 21
<212> TYPE: DNA
<213> ORGANISM: Homo sapiens

<400> SEQUENCE: 10
gccggtgctc tgaactggct g                                                21

<210> SEQ ID NO 11
<211> LENGTH: 7
<212> TYPE: PRT
<213> ORGANISM: Homo sapiens

<400> SEQUENCE: 11

Ala Gly Ala Leu Asn Trp Leu
1               5

<210> SEQ ID NO 12
<211> LENGTH: 21
<212> TYPE: DNA
<213> ORGANISM: Homo sapiens

<400> SEQUENCE: 12
gccggtgctc tgaccgggct g                                                21

```
<210> SEQ ID NO 13
<211> LENGTH: 7
<212> TYPE: PRT
<213> ORGANISM: Homo sapiens

<400> SEQUENCE: 13

Ala Gly Ala Leu Thr Gly Leu
1               5

<210> SEQ ID NO 14
<211> LENGTH: 24
<212> TYPE: DNA
<213> ORGANISM: Homo sapiens

<400> SEQUENCE: 14
tcagaaacaa aaccaaaaca aaca                                          24

<210> SEQ ID NO 15
<211> LENGTH: 19
<212> TYPE: DNA
<213> ORGANISM: Homo sapiens

<400> SEQUENCE: 15
gtcccaccag cacctaccc                                                19

<210> SEQ ID NO 16
<211> LENGTH: 20
<212> TYPE: DNA
<213> ORGANISM: Homo sapiens

<400> SEQUENCE: 16
caactgaatt tcttatctgg                                               20

<210> SEQ ID NO 17
<211> LENGTH: 20
<212> TYPE: DNA
<213> ORGANISM: Homo sapiens

<400> SEQUENCE: 17
gtaaaactgg aacgtactgg                                               20

<210> SEQ ID NO 18
<211> LENGTH: 18
<212> TYPE: DNA
<213> ORGANISM: Homo sapiens

<400> SEQUENCE: 18
atagccagac gatgaacg                                                 18

<210> SEQ ID NO 19
<211> LENGTH: 18
<212> TYPE: DNA
<213> ORGANISM: Homo sapiens

<400> SEQUENCE: 19
atggtgcagt tgagaacc                                                 18

<210> SEQ ID NO 20
<211> LENGTH: 15
<212> TYPE: DNA
<213> ORGANISM: Homo sapiens

<400> SEQUENCE: 20
```

```
gaacattttg gcagc                                                    15

<210> SEQ ID NO 21
<211> LENGTH: 19
<212> TYPE: DNA
<213> ORGANISM: Homo sapiens

<400> SEQUENCE: 21
taatggtagg cactaaagg                                                19
```

METHODS OF IDENTIFYING GENETIC MUTATIONS ASSOCIATED WITH CHARCOT-MARIE-TOOTH NEUROPATHY TYPE 1C

CROSS-REFERENCES TO RELATED APPLICATIONS

This application is a divisional of co-pending application Ser. No. 10/756,194, filed Jan. 13, 2004, which claims the benefit of Provisional Application No. 60/440,399, filed Jan. 13, 2003. The benefit of the priority of the filing dates of each application is hereby claimed under 35 U.S.C. §§120 and 119, respectively. Each application is incorporated herein by reference in its entirety.

STATEMENT OF GOVERNMENT RIGHTS

This invention was made with government support under Grant No. NS38181 awarded by the National Institutes of Health. The government has certain rights in the invention.

BACKGROUND

The present invention relates to methods and kits for identifying subjects susceptible to Charcot-Marie-Tooth Neuropathy. Charcot-Marie-Tooth (CMT) neuropathy, also called Hereditary Motor and Sensory Neuropathy (HMSN), is a clinically and genetically heterogeneous group of inherited peripheral neuropathies leading to progressive distal muscle weakness and sensory loss. CMT is frequently transmitted in an autosomal dominant manner. An estimated 1 in 2,500 persons has a form of CMT, making it a major diagnostic category within neurogenetic diseases (She, H., *Clin. Genet.* 6:98-118 (1974)). A current classification system divides CMT neuropathy into CMT type 1 (CMT1), which is characterized by demyelination and reduced nerve conduction velocities (NCVs)(typically <40 meters/sec), and CMT type 2 (CMT2), which denotes patients with axonal neuropathy, lack of myelin abnormalities in pathologic specimens, and nearly normal nerve conduction velocities (Dyck and Lambert, *Arch. Neurol.* 18:603-618 (1968)). Onset of symptoms associated with CMT typically occurs in adolescence or early adulthood; however, presentation may be delayed until mid-adulthood. The severity of symptoms is variable, even among members of the same family, with gradual progression of symptoms. Typical CMT symptoms include pes cavus, distal muscle weakness and atrophy, absent or diminished deep tendon reflexes, and mild sensory loss.

CMT1 has been divided into five subtypes (CMT1A-D, X), based on genetic linkage analysis; however, the CMT1 subtypes are clinically indistinguishable. CMT1A is associated with a 1.4 megabase (Mb) duplication on chromosome 17p11.2-p12 and a gene dosage effect for peripheral myelin protein (PMP22) (Matsumami et al., *Nat. Gen.*: 176-179 (1992)). CMT1B is associated with mutations in the myelin protein zero gene (MPZ) (Hayasaka et al., *Nat. Genet.* 5:31-34 (1993). CMT1D is associated with mutations in the early growth response 2 element gene (EGR2) (Warner et al., *Nat. Gen.* 18:382-384 (1998) and CMTX is associated with mutations in the connexin 32 (Cx32) gene (Bergoffen et al., *Science* 262:2039-2042 (1993). Recently, mutations in the ganglioside-induced differentiation-associated protein 1 gene (GDAP1) have been associated with autosomal recessive demyelinating CMT as well as autosomal recessive axonal CMT with vocal cord paralysis (Nelis, E., et al., *Neurology* 59(12):1835-6 (2002). Patients that exhibit symptoms associated with CMT1, but that lack mutations in these known genes, have been assigned to subtype CMT1C.

Given the prevalence of CMT1 cases not linked to any known genetic loci, there is a need to identify genetic mutations associated with the CMT1 syndrome that can be used in a genetic screen to identify subjects susceptible to CMT1 neuropathy. The present inventors have discovered individuals with mutations in the small integral membrane protein of the lysosome/late endosome ("SIMPLE") gene and have established a molecular linkage for CMT1C.

SUMMARY

In accordance with the foregoing, in one aspect the present invention provides methods of identifying genetic mutations that are associated with peripheral neurological disease in a mammalian subject, the methods comprising identifying a difference between a nucleic acid sequence of a small integral membrane protein of the lysosome/late endosome ("SIMPLE") gene from a first mammalian subject exhibiting peripheral neuropathy and a nucleic acid sequence of a SIMPLE gene from a second mammalian subject which is not exhibiting peripheral neuropathy, wherein the first and second mammalian subjects are members of the same species, and wherein the difference between the nucleic acid sequences is a genetic mutation that is associated with peripheral neurological disease. In some embodiments of this aspect of the invention, the method further comprises determining whether the identified mutations co-segregate with peripheral neuropathy.

In another aspect, the present invention provides isolated nucleic acid molecules encoding a SIMPLE protein comprising a missense mutation, the isolated nucleic acid molecules comprising a sequence selected from the group consisting of SEQ ID NO: 8, SEQ ID NO: 10 and SEQ ID NO: 12.

In another aspect, the present invention provides isolated SIMPLE polypeptides comprising a missense mutation, the isolated SIMPLE polypeptides comprising an amino acid sequence selected from the group consisting of SEQ ID NO: 9, SEQ ID NO: 11 and SEQ ID NO: 13.

In another aspect, the present invention provides a nucleic acid probe for detecting a SIMPLE gene consisting of a nucleic acid sequence selected from the group consisting of a nucleic acid sequence spanning nucleotide 91 to nucleotide 140 of SEQ ID NO: 4, or the complement thereof, and SEQ ID NO: 6, or the complement thereof.

In another aspect, the present invention provides nucleic acid primer molecules consisting of SEQ ID NO: 18 and SEQ ID NO: 19 which are useful for amplifying exon 3 of a SIMPLE gene.

In another aspect, the present invention provides methods of screening a mammalian subject to determine if said subject has a genetic predisposition to develop, or is suffering from Charcot-Marie-Tooth neuropathy type 1C (CMT1C). The method of this aspect of the invention comprises analyzing the nucleic acid sequence of a SIMPLE gene in a mammalian subject to determine whether a genetic mutation that is associated with CMT1C is present in the nucleic acid sequence, wherein the presence of an identified genetic mutation in the SIMPLE gene that co-segregates with CMT1C indicates that the mammalian subject has a genetic predisposition to develop CMT1C or is suffering from CMT1C.

In another aspect, the invention provides a kit for determining susceptibility or presence of CMT1C in a mammalian subject based on the detection of a mutation in a SIMPLE gene, said kit comprising (i) one or more nucleic acid primer molecules for amplification of a portion of a SIMPLE gene and (ii) written indicia indicating a correlation between the presence of said mutation and risk of developing CMT1C. In some embodiments, the kit detects the presence or absence of a mutation in the SIMPLE gene selected from the group consisting of G112S, T115N and W116G.

The invention thus provides methods, reagents and kits for identifying genetic mutations in a SIMPLE gene and thereby facilitates diagnosis of Charcot-Marie-Tooth neuropathy and identification of carriers of the genetic defect. The nucleic acid molecules of the invention are useful as probes to identify genetic mutations in the SIMPLE gene and have therapeutic utility for identifying compounds that can be used to treat Charcot-Marie-Tooth neuropathy.

DETAILED DESCRIPTION

Unless specifically defined herein, all terms used herein have the same meaning as they would to one skilled in the art of the present invention. Practitioners are particularly directed to Sambrook et al. (1989) *Molecular Cloning: A Laboratory Manual*, 2d ed., Cold Spring Harbor Press, Plainsview, N.Y., and Ausubel et al., *Current Protocols in Molecular Biology*, John Wiley & Sons, New York (1999) for definitions and terms of art.

The following definitions are provided in order to provide clarity with respect to the terms as they are used in the specification and claims to describe the present invention.

As used herein, the term "peripheral neuropathy" refers to peripheral nerve damage, including sensory and motor nerve damage, producing a variety of symptoms including for example, muscle weakness, numbness, paresthesia and pain in the arms, hands, legs and/or feet, pes cavus and reduced nerve conduction velocity.

As used herein, the term "peripheral neurological disease" refers to the clinical manifestation of a typically slowly progressive peripheral neuropathy.

As used herein, the term "paresthesia" refers to abnormal sensations such as burning, tickling, pricking or tingling.

As used herein, the term "pes cavus" refers to a deformity of the foot producing a high arch that does not flatten with weightbearing. The deformity can be located in the forefoot, midfoot, or hindfoot or in a combination of these sites.

As used herein, the term "proband" refers to the family member through whom a family's medical history comes to light.

As used herein, the term "Charcot-Marie-Tooth neuropathy" or ("CMT") refers to a peripheral (motor and sensory) neuropathy without an established acquired (non-genetic) cause as described in Sherer et al., (2003) *The Molecular and Genetic Basis of Neurological Diseases*, 3d Ed., Oxford Butterworth Hiemen Press, pp. 435-453. Unexplained chronic progressive neuropathy in individuals with a negative family history for peripheral neuropathy may represent an instance of inherited CMT on the basis of a new dominant mutation, or a single occurrence of an autosomal recessive or X-linked disorder in a family. CMT patients typically experience slowly progressive symptoms ranging from muscle weakness in the arms, legs, hands and feet, decreased muscle bulk, reduced tendon reflexes and sensory loss. Individuals with CMT may also have foot deformities, such as pes cavus, high arches, hammertoes, inverted heel, flat feet and other orthopedic problems such as mild scoliosis or hip dysplasia.

As used herein, the term "Charcot-Marie-Tooth Neuropathy type 1" or ("CMT1") includes a large group of inherited autosomal dominant disorders characterized by peripheral nerve demyelination affecting peripheral (motor and/or sensory) nerves. Hallmarks of CMT1 include reduced nerve conduction velocities (typically less than 40 meters/sec), and nerve biopsies that display "onion bulb" formation. Studies have determined that reduction in nerve conduction velocity can be accurately determined in most cases by the age of five years (Nicholson, G. A. *Neurology* 41:547-552 (1991).

As used herein, the term "Charcot-Marie Tooth Neuropathy type 1C" or ("CMT1C") refers to one of five clinically indistinguishable subtypes of Charcot-Marie-Tooth Neuropathy type 1 that is designated as type C based on the lack of molecular linkage to genetic loci associated with subtypes CMT1A, CMT1B, CMT1D, and CMT1X and/or based on the presence of mutation(s) in the SIMPLE gene.

As used herein, the term small integral membrane protein of the lysosome/late endosome "SIMPLE," also known as the lipopolysaccharide-induced TNF-alpha factor "LITAF," or p53-induced gene "PIG7" refers to any gene that encodes the SIMPLE/LITAF/PIG7 protein. Some SIMPLE genes useful in the practice of this invention are at least 90% identical to the nucleic acid sequence set forth in SEQ ID NO: 3. Some SIMPLE genes useful in the practice of this invention are at least 95%, or at least 99% identical to the nucleic acid sequence set forth in SEQ ID NO: 3.

As used herein, the term "primer" means a polynucleotide which can serve to initiate a nucleic acid chain extension reaction. Typically, primers have a length of 5 to about 50 nucleotides, although primers can be longer than 50 nucleotides.

As used herein, the term "sequence identity" or "percent identical" as applied to nucleic acid molecules is the percentage of nucleic acid residues in a candidate nucleic acid molecule sequence that are identical with a subject nucleic acid molecule sequence (such as the nucleic acid molecule sequence set forth in SEQ ID NO: 3), after aligning the sequences to achieve the maximum percent identity, and not considering any nucleic acid residue substitutions as part of the sequence identity. No gaps are introduced into the candidate nucleic acid sequence in order to achieve the best alignment. Nucleic acid sequence identity can be determined in the following manner. The subject polynucleotide molecule sequence is used to search a nucleic acid sequence database, such as the Genbank database, using the program BLASTN version 2.1 (based on Altschul et al., *Nucleic Acids Research* 25:3389-3402 (1997)). The program is used in the ungapped mode. Default filtering is used to remove sequence homologies due to regions of low complexity as defined in Wootton, J. C., and S. Federhen, *Methods in Enzymology* 266:554-571 (1996). The default parameters of BLASTN are utilized.

As used herein, the term "genetic mutation" is an alteration of the wild-type SIMPLE gene sequence deposited in GenBank, provided as SEQ ID NO: 3 that is not a recognized polymorphism. A polypmorphism typically has a population frequency of greater than 1% in mammalian control subjects of the same species that do not exhibit peripheral neuropathy.

In one aspect, the present invention provides methods of identifying genetic mutations that are associated with peripheral neurological disease in a mammalian subject. The methods of this aspect of the invention comprise the step of identifying a difference between a nucleic acid sequence of a small integral membrane protein of the lysosome/late endosome ("SIMPLE") gene from a first mammalian subject exhibiting peripheral neuropathy and a nucleic acid sequence of a SIMPLE gene from a second mammalian subject which is not exhibiting peripheral neuropathy, wherein the first and second mammalian subjects are members of the same species, and wherein the difference between the nucleic acid sequences is a genetic mutation that is associated with peripheral neurological disease. In some embodiments, the method further comprises the step of determining whether the identified genetic mutation co-segregates with peripheral neuropathy.

The methods of this aspect of the invention are useful to identify genetic mutations associated with hereditary peripheral neurological disease in any mammalian subject, particularly human subjects. For example, the methods of the invention may be used to identify genetic mutations in the SIMPLE gene that are associated (i.e., where the mutation is found to occur in subjects predisposed to develop hereditary peripheral neurological disease and the mutation is not found in subjects not predisposed to develop hereditary peripheral neurological disease) with the occurrence of hereditary peripheral neurological disease in individuals at risk for developing this disease.

The present inventors have discovered that mutations in the SIMPLE gene locus are responsible for a portion of cases of the peripheral neurological disease Charcot-Marie-Tooth Neuropathy type 1C (CMT1C). Previously, patients were designated as subtype CMT1C based on the absence of mutations in genetic loci known to be associated with CMT1, such as the peripheral myelin protein 22 (PMP22) gene (associated with CMT1A), the myelin protein zero gene (MPZ) (associated with CMT1B), the early growth response 2 element gene (EGR2) (associated with CMT1D) or the connexin 32 (Cx32) (associated with CMTX). SIMPLE was identified as a candidate gene for CMT1C based in part on chromosomal mapping to a 9 cM region on chromosome 16p as described in Example 1.

The SIMPLE gene appears to be almost ubiquitously expressed (Moriwaki et al., *J. Biol Chem* 276:23065-23076 (2001), however the biological function of the SIMPLE protein is currently unknown. The protein encoded by the SIMPLE gene possesses a putative membrane association domain flanked by two putative CXXC motifs, known as high affinity zinc binding motifs (Collet et al., *J. Biol. Chem* 2:2, (2003). In addition, the N-terminus of the SIMPLE protein contains two PPXY motifs (WW domain binding motif) that have been shown to interact with Nedd4, an E3 ubiquitin ligase that plays a role in ubiquitinating membrane proteins (Jolliffe et al., *Biochem J* 351:557-565 (2000)). The SIMPLE protein is identical to a protein previously described as lipopolysaccharide-induced TNF-alpha factor ("LITAF"). Moriwaki et al., *J. Biol Chem* 276:23065-23076 (2001). LITAF was originally cloned as a putative nuclear transcription factor involved in binding to a critical region of the TNF-alpha promoter (Myokai et al., *Proc Natl Acad Sci* 96:4518-4523 (1999)).

The human SIMPLE gene consists of four exons spanning a genomic interval of 37.75 kilobases, with a start codon located in exon 2. The SIMPLE cDNA coding sequence is provided herein as SEQ ID NO: 1 which corresponds to nucleotides 234-719 of GenBank accession number AB034747. Disclosed herein are nucleic acid mutations numbered sequentially with respect to the first nucleotide of SEQ ID NO: 1. The SIMPLE protein encoded by SEQ ID NO: 1 is provided herein as SEQ ID NO: 2. Disclosed herein are amino acid mutations numbered sequentially with respect to the first amino acid residue of SEQ ID NO: 2. The entire 37.75 kilobase genomic locus that encompasses the SIMPLE gene is provided herein as SEQ ID NO: 3. With respect to the first nucleotide in SEQ ID NO: 3, the four exons are as follows: exon 1: nucleotides 1 to 228; exon 2: nucleotides 29,639 to 29,863; exon 3: nucleotides 32,685 to 32,840; and exon 4: nucleotides 36,629 to 37,775. The start codon is in exon 2 at nucleotide 29,644. The nucleic acid sequence encoding exon 3 (nucleotides 29,639 to 29,863 of SEQ ID NO: 3) is provided herein as SEQ ID NO: 4, which encodes the amino acid sequence provided as SEQ ID NO: 5.

The present inventors have identified several missense mutations (for example, G112S, T115N and W116G) in SIMPLE that cause a portion of CMT1C cases. The patients with these mutations in SIMPLE (as further described in Examples 1 and 2) exhibited peripheral neuropathy and met widely accepted criteria for CMT1 including distal muscle weakness and atrophy, depressed deep tendon reflexes and sensory impairment (see Dyck, P. J., and E. H. Lambert, *Arch. Neurol.* 18:619-625 (1968)). The three missense mutations G112S, T115N, and W116G are clustered in a conserved region of exon 3 encompassing seven amino acids as shown in Table 1. The amino acid sequence of the wild-type human SIMPLE protein AGALTWL (SEQ ID NO: 7) is identically conserved in human, mouse, rat and chicken (Street et al., *Neurology* 60:22-27). As shown in Table 1, the tight clustering of mutations within exon 3 of the SIMPLE gene suggest this domain, which is immediately adjacent to a membrane association domain, is critical to peripheral nerve function. The first column of Table 1 provides the CMT1 pedigree from which each mutant was identified. The second column provides the altered (underlined) amino acid residue in each CMT1 pedigree.

TABLE 1

CONSERVED AMINO ACID REGION OF THE SIMPLE
PROTEIN CONTAINING MISSENSE MUTATIONS

| CMT1 Pedigree/ Mutation | Nucleic Acid Sequence | Amino Acid Sequence |
| --- | --- | --- |
| Wild-type human | GCCGGTGCTCTGACCTGGCTG SEQ ID NO: 6 | AGALTWL SEQ ID NO: 7 |
| K1551, K1552, PN282 G112S | GCC<u>A</u>GTGCTCTGACCTGGCTG SEQ ID NO: 8 | A<u>S</u>ALTWL SEQ ID NO: 9 |
| K1550 T115N | GCCGGTGCTCTGA<u>A</u>CTGGCTG SEQ ID NO: 10 | AGAL<u>N</u>WL SEQ ID NO: 11 |
| K2900, K1910 W116G | GCCGGTGCTCTGACC<u>G</u>GGCTG SEQ ID NO: 12 | AGALT<u>GL</u> SEQ ID NO: 13 |

The practice of this aspect of the invention is therefore useful to identify additional mutations in the SIMPLE gene that are associated with peripheral neurological diseases such as, for example, CMT (type 1 or type 2), Dejerine-Sottas disease, congenital hypomyelination neuropathy, and hereditary neuropathy with liability to pressure palsies. By way of illustrative example, Dejerine-Sottas disease (DSD) is a peripheral neurological disease with clinical features that overlap with those of severe CMT1. Molecular studies indicate that DSD, like CMT, shows genetic heterogeneity and shares several genetic loci in common with those implicated for CMT1, including PMP22, MPZ and EGR2, as well as periaxin (PRX) (Boerkoel et al., *Am J Hum Genet* 68: 325-33 (2001). Therefore, the methods of this aspect of the invention may be used to identify genetic mutations in SIMPLE that are associated with Dejerine-Sottas disease or other peripheral neurological diseases. In some patients with peripheral neuropathy, mutations in SIMPLE may occur in combination with a mutation in another gene known to be associated with peripheral neurological disease, such as, for example, PMP22, Cx32, MPZ, EGR2, GDAP, and PRX as described herein. For example, mutations in the SIMPLE gene may act to increase or decrease the clinical severity of a peripheral neurological disease that has previously been associated with a mutation in a gene other than SIMPLE.

In the practice of this aspect of the method of the invention, any method of obtaining reliable nucleic acid sequence data from a mammalian subject exhibiting peripheral neuropathy may be utilized. For example, reliable sequence data may be obtained from existing databases of sequence data, or alternatively, a reliable nucleic acid assay that will identify a genetic mutation in the SIMPLE gene may be utilized.

In one embodiment of the method of the invention, a genetic mutation is detected by amplification of all or part of the SIMPLE gene from genomic DNA followed by sequencing of the amplified DNA. For example, each of the four exons of the SIMPLE gene may be amplified individually or in combination using as template genomic DNA from a test subject exhibiting peripheral neuropathy. A method of amplification which is well known by those skilled in the art is the polymerase chain reaction (PCR) (see *Current Protocols in Molecular Biology*, Ausubel, F. M. et al., John Wiley & Sons; 1995). Alternative amplification techniques may also be used in the method of this aspect of the invention, such as the ligase chain reaction (LCR) (Wu and Wallace, *Genomics* 4:560-569 (1989)), strand displacement amplification (SDA) (Walker et al., *Proc. Nat'l. Acad. Sci. USA* 89:392-396 (1992)), self-sustained sequence replication (3SR) (Fahy et al., *PCR Methods Appl.* 1:25-33 (1992)), and branched chain amplification which are known and available to persons skilled in the art.

The PCR process involves the use of pairs of primers, one for each complementary strand of the duplex DNA (wherein the coding strand is referred to as the "sense strand" and its complementary strand is referred to as the "anti-sense strand"), that will hybridize at sites located on either side of a region of interest in a gene. Chain extension polymerization is then carried out in repetitive cycles to increase the number of copies of the region of interest exponentially. Primers useful in the practice of the method of the invention comprise polynucleotides that hybridize to a region of a SIMPLE gene, which can serve to initiate a chain extension reaction. A "primer pair" is a pair of primers which specifically hybridize to sense (coding) and antisense (non-coding) strands of a duplex polynucleotide to permit amplification of the region lying between the primers of the pair. Primers useful in the practice of this aspect of the invention comprise a polynucleotide of any size that is capable of hybridizing to SEQ ID NO: 1, SEQ ID NO: 3 or SEQ ID NO: 4 under conditions suitable for PCR amplification and/or sequencing. In a preferred embodiment, primers useful in the practice of this aspect of the invention range from about 5 to 50 bp or longer of continuous sequence chosen from SEQ ID NO: 1, SEQ ID NO: 3, or SEQ ID NO: 4. Table 2 describes sets of primers useful for PCR amplifying and sequencing of each of the four exons of the SIMPLE gene from genomic DNA. The first column of Table 2 describes the exon to be amplified and the second column and third columns provide the nucleotide sequence of the forward and reverse primers used to amplify the exon and their corresponding SEQ ID NOs. Tm refers to the melting temperature of the oligonucleotide pair. The expected PCR product size in base pairs (bp) for each PCR amplification is provided in the fifth column. Example 1 provides a non-limiting example of this embodiment of the method of the invention.

TABLE 2

PRIMERS FOR EXON FRAGMENT AMPLIFICATION AND SEQUENCING OF THE SIMPLE GENE

| Exon | Forward Primer | Reverse Primer | Tm | Size bp |
|---|---|---|---|---|
| 1 | 1F 5' TCAGAAACAAAACCA-AAACAAACA 3' (SEQ ID NO: 14) | 1R 5' GTCCCACCAGCACCTACCC 3' (SEQ ID NO: 15) | 59.7 | 337 |
| 2 | 2F 5' CAACTGAATTTCTTATCT-GG 3' (SEQ ID NO: 16) | 2R 5' GTAAAACTGGAACGTACTGG 3' (SEQ ID NO: 17) | 55 | 387 |
| 3 | 3F 5' ATAGCCAGACGATGA-ACG 3' (SEQ ID NO: 18) | 3R 5' ATGGTGCAGTTGAGAACC 3' (SEQ ID NO: 19) | 53 | 385 |
| 4 | 4F 5' GAACATTTTGGCAGC 3' (SEQ ID NO: 20) | 4R 5' TAATGGTAGGCACTAAAGG 3' (SEQ ID NO: 21) | 59 | 636 |

In one embodiment of the method of the invention, after amplification, genetic mutations are detected in the amplified DNA by sequence analysis. Methods of DNA sequence analysis are well known in the art. A well known method of sequencing is the "chain termination" method first described by Sanger et al., *PNAS (USA)* 74(12):5463-5467 (1977) and detailed in SEQUENASE™ 2.0 product literature (Amersham Life Sciences, Cleveland). Sequencing can be performed using a single primer or a primer pair. Primers are chosen for sequencing based on their proximity to the region of interest. Non-limiting examples of suitable sequencing primers for each exon are described in Table 2.

Once the nucleic acid sequence from the test subject is obtained, the sequence is compared to the nucleic acid sequence of one or more subjects not exhibiting peripheral neuropathy in order to identify genetic mutations in SIMPLE that are associated with peripheral neurological disease. For example, resulting sequences can be aligned with the known exon sequence using a multiple sequence alignment tool, Sequencher (Gene Codes Corporation, Ann Arbor, Mich.), in order to identify any nucleotide changes as described in Example 5. In one embodiment, the information and analysis can be recorded on a database and the comparisons can be performed by a computer system accessing said database. In this manner, the amplified sequences of SIMPLE from a subject exhibiting peripheral neurological disease are sequenced until a mutation in SIMPLE associated with peripheral neurological disease is identified.

A mutation associated with peripheral neurological disease encompasses any alteration of the wild-type small integral membrane protein of the lysosome/late endosome ("SIMPLE") sequence deposited in GenBank, provided as SEQ ID NO: 3, that is not a recognized polymorphism. A polymorphism typically has a population frequency of greater than 1% in mammalian control subjects of the same species that do not exhibit peripheral neuropathy, and is not associated with peripheral neurological disease. In contrast, a mutation that is positively associated with peripheral neurological disease typically co-segregates with family members exhibiting peripheral neuropathy. The following characteristics are supportive, but are not required for a genetic mutation to be a causative mutation for peripheral neurological disease: (1) the change results in an amino acid substitution in a highly evolutionarily conserved residue of the SIMPLE protein (such as in exon 3 (SEQ ID NO: 5) or in the conserved region of exon 3 (SEQ ID NO: 7); (2) the change occurs in a functional domain of SIMPLE; (3) the change is predicted to affect splicing; or (4) the change co-segregates with disease in a family in an autosomal dominant manner.

A genetic mutation may be any form of sequence alteration including a deletion, insertion, point mutation or DNA rearrangement in the coding or noncoding regions. Deletions may be small or large and may be of the entire gene or of only a portion of the gene. Point mutations may result in stop codons, frameshift mutations or amino acid substitutions. Point mutations may also occur in regulatory regions, such as in the promoter of the SIMPLE gene, leading to loss or diminution of expression of the mRNA. Point mutations may also abolish proper RNA processing, leading to loss of expression of the SIMPLE gene product, or to a decrease in mRNA stability or translation efficiency. DNA rearrangements include a simple inversion of a single segment of DNA, a reciprocal or nonreciprocal translocation disrupting any portion of the gene, or a more complex rearrangement.

In one embodiment of this aspect of the method of the invention, once a mutation is identified in a subject exhibiting peripheral neuropathy, co-segregation analysis is carried out to determine if the particular mutation in the SIMPLE gene co-segregates with the presence of peripheral neuropathy in the subjects tested. The standard test for genetic linkage is described in J. Ott (1999), *Analysis of Human Genetic Linkage,* 3d ed., The Johns Hopkins University Press. Co-segregation analysis can be done in several ways. In one embodiment, co-segregation analysis is done by sequencing DNA amplified from the corresponding exon in subjects exhibiting peripheral neuropathy utilizing the previously described methods. For example, DNA sequence variations can be identified using DNA sequencing, as described in Example 1. Alternatively, there are several other methods that can be used to detect and confirm DNA sequence variation including, for example, (1) restriction fragment length polymorphism (RFLP) analysis as described in Example 3; (2) single stranded conformation analysis (SSCA) (Orita et al., *Proc. Nat'l. Acad. Sci. USA* 86:2776-2770 (1989)); (3) denaturing gradient gel electrophoresis (DGGE) based on the detection of mismatches between the two complementary DNA strands (Wartell et al., *Nucl. Acids Res.* 18:2699-2705 (1990)); (4) RNase protection assays (Finkelstein et al., *Genomics* 7:167-172 (1990)); (5) hybridization with allele-specific oligonucleotides (ASOs) (Conner et al., *Proc. Nat'l. Acad. Sci. USA* 80:278-282 (1983)); and (6) allele-specific PCR (Rano & Kidd, *Nucl. Acids Res.* 17:8392 (1989)). In the SSCA, DGGE and RNase protection assay, a new electrophoretic band appears when a mutation is present. SSCA detects a band which migrates differently because the sequence change causes a difference in single-strand, intramolecular base pairing. DGGE detects differences in migration rates of mutant sequences compared to wild-type sequences using a denaturing gradient gel. For allele-specific PCR, primers are used which hybridize at their 3' ends to a particular SIMPLE mutation. If the particular SIMPLE mutation is not present, an amplification product is not observed. Insertions and deletions of genes can also be detected by cloning, sequencing and amplification.

In another embodiment, genetic mutations are identified by hybridization of amplified regions of the SIMPLE gene with allele-specific oligonucleotides. For example, a hybridization assay may be carried out by isolating genomic DNA from a mammalian subject exhibiting peripheral neuropathy, contacting the isolated DNA with a hybridization probe specific for a SIMPLE gene mutation under conditions suitable for hybridization of the probe with the isolated genomic DNA, said DNA probe spanning said mutation in said gene, wherein said DNA probe is capable of detecting said mutation; and determining the presence or absence of said hybridized DNA probe as an indication of the presence or absence of said genetic mutation. Desirable probes useful in such a DNA hybridization assay comprise a nucleic acid sequence that is unique to the genetic mutation. Examples of useful DNA probes include SEQ ID NO: 6; SEQ ID NO: 8; SEQ ID NO: 10 and SEQ ID NO: 12 as provided in Table 1. Analysis can involve denaturing gradient gel electrophoresis or denaturing HPLC methods, for example. For guidance regarding probe design and denaturing gel electrophoresis or denaturing HPLC methods, see, e.g., Ausubel et al., 1989, *Current Protocols in Molecular Biology*, Green Publishing Associates and Wiley Interscience, N.Y.

In another embodiment of this aspect of the method of the invention, restriction fragment length polymorphism (RFLP) for the SIMPLE gene can be used to score for a genetic mutation in a co-segregation analysis. RFLP has been described in U.S. Pat. Nos. 4,965,188 and 4,800,159, incorporated herein by reference. In this technique, restriction enzymes are used which provide a characteristic pattern of restriction fragments, wherein a restriction site is either missing or an additional restriction site is introduced in the mutant allele. Thus, DNA from an individual and from control DNA sequences are isolated and subjected to cleavage by restriction enzymes which are known to provide restriction fragments which differentiate between normal and mutant alleles, and the restriction patterns are identified. Example 3 and Table 4 further illustrate RFLP methods that are useful in the practice of the method of the invention.

Several genetic mutations in SIMPLE that are associated with the peripheral neurological disease CMT1 have been identified by practicing the methods of this aspect of the invention as described in Examples 1 and 2 and shown in Tables 1 and 3. Table 3 provides a list of mutations identified in a SIMPLE gene using the methods of this aspect of the invention. The first column of Table 3 describes the exon each mutation resides in, the second column describes the nucleotide change in the cDNA (numbered sequentially with reference to SEQ ID NO: 1) for each mutant, the third column describes the type of mutation that is present, the fourth column describes primer pairs useful to PCR amplify the exon containing the mutation, and the fifth column describes primers useful for sequencing across the region containing the mutation.

TABLE 3

SUMMARY OF MUTATIONS IDENTIFIED IN THE SIMPLE GENE THAT CO-SEGREGATE WITH PERIPHERAL NEUROPATHY

| Exon | Nucleotide change in cDNA | Predicted amino acid change in protein | Type of Mutation | Primers used to PCR amplify | Primers used to sequence |
|---|---|---|---|---|---|
| 3 | 334G to A | G112S | missense | 3F (SEQ ID NO: 18) 3R (SEQ ID NO: 19) | 3F (SEQ ID NO: 18) |
| 3 | 344C to A | T115N | missense | 3F (SEQ ID NO: 18) 3R (SEQ ID NO: 19) | 3F (SEQ ID NO: 18) |
| 3 | 346T to G | W116G | missense | 3F (SEQ ID NO: 18) 3R (SEQ ID NO: 19) | 3F (SEQ ID NO: 18) |

In another aspect, the present invention provides isolated nucleic acid molecules encoding a SIMPLE protein comprising a mutation selected from the group consisting of G112S, T115N, and W116G. The mutations in the SIMPLE protein are numbered sequentially according to the first amino acid of SEQ ID NO: 2. The nucleotide sequences are numbered sequentially according to the first nucleotide of SEQ ID NO: 1. Each mutation is further described as follows:

Mutation G112S results from a nucleotide change of G to A at nucleotide 334, which results in a codon change from GGT to AGT which in turn results in the missense mutation at amino acid G112 to S, substituting a serine for a glycine at amino acid position 112 in the SIMPLE protein. In some embodiments, mutation G112S is encoded by SEQ ID NO: 8 as shown in Table 1.

Mutation T115N results from a nucleotide change of C to A at nucleotide 344, which results in a codon change from ACC to AAC which in turn results in the missense mutation at amino acid T115 to N, substituting an asparagine for a threonine at amino acid position 115 in the SIMPLE protein. In some embodiments, mutation T115N is encoded by SEQ ID NO: 10 as shown in Table 1.

Mutation W116G results from a nucleotide change of T to G at nucleotide 346, which results in a codon change from TGG to GGG which in turn results in the missense mutation at amino acid W116 to G, substituting a glycine for a tryptophan at amino acid position 116 in the SIMPLE protein. In some embodiments, mutation W116G is encoded by SEQ ID NO: 12 as shown in Table 1.

In some embodiments, the isolated nucleic acid molecules described herein comprise a sequence selected from the group consisting of SEQ ID NO: 8, SEQ ID NO: 10, and SEQ ID NO: 12. In this regard, in some embodiments, the isolated nucleic acid molecules described herein are at least 90% identical to a portion of SEQ ID NO: 1 or its complement. In some embodiments, the isolated nucleic acid molecules described herein are at least 90% identical to a portion of SEQ ID NO: 3 or its complement. In some embodiments, the isolated nucleic acid molecules described herein are at least 90% identical to a portion of SEQ ID NO: 4 or its complement. In some embodiments, the isolated nucleic acid molecules described herein are at least 90% identical to an isolated nucleic acid molecule selected from the group consisting of SEQ ID NO: 6, SEQ ID NO: 8, SEQ ID NO: 10, and SEQ ID NO: 12 as described in Table 1. In some embodiments, the isolated nucleic acid molecules described herein hybridize to the complement of SEQ ID NO: 1 under conditions of 5×SSC at 50° C. for 1 hr. In some embodiments, the isolated nucleic acid molecules described herein hybridize to the complement of SEQ ID NO: 1 under conditions of 5×SSC at 60° C. for 1 hr. In some embodiments, the isolated nucleic acid molecules described herein hybridize to the complement of SEQ ID NO: 3 under conditions of 5×SSC at 50° C. for 1 hr. In some embodiments, the isolated nucleic acid molecules described herein hybridize to the complement of SEQ ID NO: 3 under conditions of 5×SSC at 60° C. for 1 hr. In some embodiments, the isolated nucleic acid molecules described herein hybridize to the complement of SEQ ID NO: 4 under conditions of 5×SSC at 50° C. for 1 hr. In some embodiments, the isolated nucleic acid molecules described herein hybridize to the complement of SEQ ID NO: 4 under conditions of 5×SSC at 60° C. for 1 hr.

Some nucleic acid embodiments, for example, include genomic DNA, RNA, and cDNA encoding the mutant proteins or fragments thereof. In some embodiments, the invention also encompasses DNA vectors such as, for example DNA expression vectors that contain any of the foregoing nucleic acid sequences operatively associated with a regulatory element that directs the expression of the coding sequences the nucleic acids above, and genetically engineered host cells that contain any of the foregoing nucleic acid sequences operatively associated with a regulatory element that directs the expression of the coding sequences in the host cell. The nucleic acids encoding the SIMPLE protein mutations can be manipulated using conventional techniques in molecular biology so as to create recombinant constructs that express mutant polypeptides.

The nucleic acid sequences described above have diagnostic as well as therapeutic use. The nucleic acid sequences can be used as probes to identify more genetic mutations in the SIMPLE gene and to detect the presence or absence of wild-type or mutant genes in an individual, such as in nucleic acid hybridization assays, southern and northern blot analysis, and as controls for screening assays and the kits described herein. The sequences described herein can also be incorporated into constructs for preparing recombinant mutant proteins or used in methods of searching or identifying agents that modulate SIMPLE levels and/or activity, for example, candidate therapeutic agents. For example, agents that modulate SIMPLE levels may be utilized to treat diseases of the nervous system. Because the mutations of this aspect of the invention are dominant negative or gain of function mutations, they have also have therapeutic utility for use in the identification and development and design of drugs which circumvent or overcome the mutated SIMPLE gene function. The sequences of the nucleic acids and/or proteins described herein can also be incorporated into computer systems and used with modeling software so as to enable rational drug design. Information from genotyping methods provided herein can be used, for example, in computer systems, in pharmacogenomic profiling of therapeutic agents to predict effectiveness of an agent in treating an individual for a neurological disease.

The identification of mutants T115N and G112S is described in Example 1. The identification of mutant W116G is described in Example 2. The co-segregation analysis of these mutations is described in Example 3 and Table 4. Further characterization of these mutations is described in Tables 1 and 3.

In another aspect, the invention provides a nucleic acid probe for detecting a SIMPLE gene, the probe consisting of a nucleic acid sequence selected from the group consisting of nucleotide 91 to nucleotide 140 of SEQ ID NO: 4, or the complement thereof and SEQ ID NO: 6, or the complement thereof. The nucleic acid probes of this aspect of the invention are useful to detect the presence of a wild-type gene in an individual, such as in nucleic acid hybridization assays, southern and northern blot analysis and as controls for the screening assays and kits described herein. The nucleic acid probes of this aspect of the invention may be used in nucleic acid hybridization assays with genomic DNA isolated from a mammalian subject as described herein.

In another aspect, the invention provides nucleic acid primer molecules consisting of sequence SEQ ID NO: 18 and SEQ ID NO: 19. The primer molecules of the invention can be used individually as sequencing primers, or together as a primer pair for amplifying exon 3 of the SIMPLE gene, under conditions as disclosed in Table 2. SEQ ID NO: 18 and SEQ ID NO: 19 can be used, for example, to screen for mutations in the SIMPLE gene that are associated with peripheral neuropathy and are useful reagents in the methods and kits described herein.

In another aspect, the invention provides isolated mutant SIMPLE polypeptides and peptide fragments. Mutant SIMPLE polypeptides are SIMPLE proteins encoded by a SIMPLE gene having at least one of the mutations associated with peripheral neuropathy, as described above. In some embodiments, the isolated polypeptide includes mutation G112S, such as, for example, an isolated polypeptide comprising SEQ ID NO: 9. In other embodiments, the isolated polypeptide includes mutation T115N, such as, for example, an isolated polypeptide comprising SEQ ID NO: 11. In further embodiments, the isolated polypeptide includes mutation W116G, such as, for example, an isolated polypeptide comprising SEQ ID NO: 13. The isolated mutant SIMPLE polypeptides and peptide fragments are useful, for example, as antigens for raising antibodies which specifically bind to mutant SIMPLE polypeptides.

In another aspect, the present invention provides methods of screening a mammalian subject to determine if said subject has a genetic predisposition to develop, or is suffering from Charcot-Marie-Tooth type 1C (CMT1C) neuropathy. The methods of this aspect of the invention comprise the step of analyzing the nucleic acid sequence of a SIMPLE gene in a subject to determine whether a genetic mutation that is associated with CMT1C is present in the nucleic acid sequence, wherein the presence of such a mutation indicates that the mammalian subject has a genetic predisposition to develop CMT1C or is diagnosed as suffering from such a disease. In some embodiments, the method further comprises determining whether the mammalian subject is exhibiting peripheral neuropathy. The clinical examination of a mammalian subject for symptoms related to peripheral neuropathy may be done either prior to, or after nucleic acid analysis of the test subject.

The method of this aspect of the invention is useful for screening any mammalian subject, such as for example, a human subject, for the genetic predisposition to develop CMT1C disease. The method is useful for preimplantation, prenatal and postnatal diagnosis of neurological disease caused by mutation in the SIMPLE gene that facilitates genetic counseling and therapeutic intervention. The method is especially useful for screening and diagnosing presymptomatic at-risk family members for the presence or absence of mutations in SIMPLE associated with the disease. The method is also useful for screening subjects exhibiting peripheral neuropathy to determine whether their symptoms are caused by a genetic mutation in the SIMPLE gene.

Any genetic mutation in the SIMPLE gene that co-segregates with CMT1C is useful in the practice of the method of this aspect of the invention. Examples of such mutations are shown in Table 3. In one embodiment, genetic mutations that co-segregate with CMT1C are missense mutations in which a nucleic acid base change results in an amino acid substitution in the SIMPLE protein. Examples of such missense mutations include, for example, G112S, T115N, and W116G as shown in Table 3.

In another embodiment, the method of this aspect of the invention can be practiced using mutations that cause deletions or silent mutations which do not alter the amino acid sequence, but may change splicing or gene regulation.

In some embodiments of the invention, subjects are screened for genetic mutations at one or more of the SIMPLE protein positions: 111, 112, 113, 114, 115, or 116.

In some embodiments of this aspect of the method of the invention, subjects are screened for the presence of a genetic mutation that is associated with CMT1C disease in exon 3 of a SIMPLE gene, such as, for example, nucleotides 32,685 to 32,840 of SEQ ID NO: 3. Exon 3 encodes a region of highly conserved amino acid residues as shown in Table 1, provided as SEQ ID NO: 7. Examples of mutations found in exon 3 within the highly conserved region of SEQ ID NO: 7 that co-segregate with CMT1C are shown in Table 1 and include G112S, T115N, and W116G.

Individuals carrying particular mutations in the SIMPLE gene may be identified using a variety of techniques of analyzing nucleic acid sequence that are well known in the art such as, for example, direct sequencing, PCR amplification and sequencing, restriction fragment length polymorphism (RFLP), nucleic acid hybridization, and single strand conformation polymorphism (SSCP). For each of these techniques, the test subject provides a biological sample containing genomic DNA to be analyzed. The test sample may be obtained from body cells, such as those present in peripheral blood, cheek cells, urine, saliva, surgical specimen, and autopsy specimens. The test sample can be processed to inactivate interfering compounds, and to purify or partially purify the nucleic acids in the sample. Any suitable purification method can be employed to obtain purified or partially purified nucleic acids from the test sample. A lysing reagent optionally can be added to the sample, particularly when the nucleic acids in the sample are sequestered or enveloped, for example, by cellular or nuclear membranes. Additionally, any combination of additives, such as buffering reagents, suitable proteases, protease inhibitors, nucleases, nuclease inhibitors and detergents can be added to the sample to improve the amplification and/or detection of the nucleic acids in the sample. Additionally, when the nucleic acids in the sample are purified or partially purified, the use of precipitation can be used, or solid support binding reagents can be added to or contacted to the sample, or other methods and/or reagents can be used. One of ordinary skill in the art can routinely select and use additives for, and methods for preparation of a nucleic acid sample for amplification.

In one embodiment of the method of the invention, the nucleic acid sequence is analyzed by direct sequencing for differences in nucleic acid sequence from the wild-type SIMPLE gene by sequencing of the subject's SIMPLE gene using primers specific for the region of interest, such as, for example, the sequencing primers described in Table 2 and Table 3.

In another embodiment, prior to sequencing the DNA is amplified enzymatically in vitro through use of PCR (Saiki et al., *Science* 239:487-491 (1988)) or other in vitro amplification methods as previously described herein. In a further embodiment, the DNA from an individual can be evaluated using RFLP techniques are described in Example 3 and elsewhere herein. The previously described methods useful for determining co-segregation analysis are also useful in this aspect of the method of the invention, such as, for example, nucleic acid hybridization techniques and single strand conformation polymorphism (SSCP). SSCP is a rapid and sensitive assay for nucleotide alterations, including point mutations (see Orita, M., et al., *Genomics* 5:874-879 (1989)). DNA segments ranging in length from approximately 100 bp to approximately 400 bp are amplified by PCR, heat denatured and electrophoresed on high resolution-non-denaturing gels. Under these conditions, each single-stranded DNA fragment assumes a secondary structure determined in part by its nucleotide sequence. Even single base changes can significantly affect the electrophoretic mobility of the PCR product.

In another aspect, the present invention provides kits for determining susceptibility or presence of CMT1C in a subject. The kits of the invention include (i) one or more nucleic acid primer molecules for amplification of a portion of the SIMPLE gene; and (ii) written indicia indicating a correlation between the presence of said mutation and risk of developing CMT1C. In one embodiment, the kits of the invention further comprise means for determining whether a mutation associated with CMT1C is present. In some embodiments, the kits of the invention comprise detection components specific for one or more of the particular genetic mutations described herein.

Primer molecules for amplification of a portion of the SIMPLE gene can be of any suitable length and composition and are selected to facilitate amplification of at least one or more regions (in the case of duplexed or multiplexed amplification) of the SIMPLE gene as shown in SEQ ID NO: 3 that potentially contains a genetic mutation. For example, oligonucleotide primers can be in the range of 5 bp to 50 bp or longer, and are chosen as primer pairs so that primers hybridize to sequences flanking the putative mutation. Primer pairs typically have an annealing temperature within about 20° C. of each other. Computer programs are useful in the design of primers with the required specificity and optimal amplification properties. See, e.g., Oligo version 5.0 (available from National Biosciences Inc., 3001 Harbor Lane, Suite 156, Plymouth, Minn.). Examples of primer pairs suitable for inclusion in the kit of the invention are provided in Table 2.

Similarly, a kit of the invention can also provide reagents for a duplexed amplification reaction (with two pairs of primers) a multiplexed amplification reaction (with three or more pair of primers) so as to amplify multiple sites of SIMPLE nucleotide mutations in one reaction.

Also included in the kit of the invention are written indicia indicating a correlation (typically a positive correlation) between the presence of a particular mutation in the SIMPLE gene and the risk of developing CMT1C disease.

The kit optionally also comprises one or more enzymes useful in the amplification or detection of nucleic acids and/or nucleotide sequences. Suitable enzymes include DNA polymerases, RNA polymerases, ligases, and phage replicases. Additional suitable enzymes include kinases, phosphatases, endonucleases, exonucleases, RNAses specific for particular forms of nucleic acids (including, but not limited to, RNAse H), and ribozymes. Other suitable enzymes can also be included in the kit.

The kit optionally comprises amplification reaction reagents suitable for use in nucleic acid amplification. Such reagents are well known and include, but are not limited to: enzyme cofactors such as magnesium or manganese; salts; nicotinamide adenine dinucleotide (NAD), and deoxynucleoside triphosphates (dNTPs). The kit optionally can also comprise detection reaction reagents, such as light or fluorescence generating substrates for enzymes linked to probes.

The kit optionally includes control DNA, such as positive and negative control samples. Negative control samples may comprise for example, genomic DNA or SIMPLE cDNA from a mammalian subject with no predisposition to CMT1C, or portions thereof. Positive control samples may comprise, for example, nucleic acid molecules containing an identified mutation in the SIMPLE gene as described herein.

The kit optionally includes instructions for using the kit in the detection of mutations in SIMPLE associated with CMT1C disease. The kit also preferably includes instructions on the appropriate parameters for the amplification reaction. Any suitable set of amplification parameters can be employed. For example, the precise temperature at which double-stranded nucleic acid sequences dissociate, primers hybridize or dissociate, and polymerase is active, are dependent on the length and composition of the sequences involved, the salt content of the reaction, the oligonucleotide concentration, the viscosity of the reaction and the type of polymerase. One of ordinary skill in the art can easily determine appropriate temperatures for the amplification reaction (see, e.g., Wetmur, *J. Critical Reviews in Biochemistry and Molecular Biology* 26:227-59 (1991)). For example, temperatures above about 90° C., such as between about 92° C., and about 100° C., are typically suitable for the dissociation of double-stranded nucleic acid sequences. Temperatures for forming primer hybrids are preferably between about 45° C. and about 65° C. Temperatures for the polymerization/extension phase are typically between about 60° C. and about 90° C., depending on the polymerase utilized in the reaction.

A multiplicity of suitable methods may be used to analyze the amplified nucleic acid product to determine whether a mutation associated with CMT1C disease is present. Suitable means include DNA sequencing, northern blotting, southern blotting, Southwestern blotting, probe shift assays (see, e.g., Kumar et al., *AIDS Res. Hum. Retroviruses* 5:345-54 (1989), T4 Endonuclease VII-mediated mismatch-cleavage detection (see, e.g., Youil et al., *Proc. Nat'l. Acad. Sci. USA* 92:87-91 (1995), Fluorescence Polarization Extension (FPE), Single Strand Length Polymorphism (SSLP), PCR-Restriction Fragment Length Polymorphism (PCR-RFLP), Immobilized Mismatch Binding Protein Mediated (MutS-mediated) Mismatch detection (see, e.g., Wagner et al., *Nucleic Acids Research* 23:3944-48 (1995), reverse dot blotting, (see, e.g., European Patent Application No. 0 511 559), hybridization-mediated enzyme recognition (see, e.g., Kwiatkowski et al., *Mol. Diagn.* 4(4):353-64 (1999)), describing the Invader™ embodiment of this technology by Third-Wave Technologies, Inc.), detection, single-strand conformation polymorphism (SSCP) and gradient denaturing gel electrophoresis to detect probe-target mismatches (e.g., "DGGE", see, e.g., Abrams et al., Genomics 7:463-75 (1990), Ganguly et al., *Proc. Nat'l. Acad. Sci. USA* 90:10325-29 (1993), and Myers et al., *Methods Enzymology* 155:501-27 (1987)).

The kit is preferably provided in a microbiologically stable form. Microbiological stability can be achieved by any suitable means, such as by (i) freezing, refrigeration, or lyophilization of kit components; (ii) by heat-, chemical-, or filtration-mediated sterilization or partial sterilization; and/or (iii) by the addition of antimicrobial agents such as azide, detergents, and other suitable reagents to other kit components. The kit can also be optionally provided in a suitable housing that is preferably useful for robotic handling by a clinically useful sample analyzer. For example, the kit can optionally comprise multiple liquids, each of which are stored in distinct compartments within the housing. In turn, each compartment can be sealed by a device that can be removed, or easily penetrated, by a mechanical device.

The following examples merely illustrate the best mode now contemplated for practicing the invention, but should not be construed to limit the invention. All literature citations herein are expressly incorporated by reference Example 1

This example describes the identification of the T115N and the G112S missense mutations in the SIMPLE gene and demonstrates that these mutations co-segregate with Charcot-Marie-Tooth neuropathy type 1C.

Mapping an Autosomal Dominant Charcot-Marie-Tooth Neuropathy to Chromosome 16p

Subjects:

A four generation family of Irish descent comprising 37 family members, some of which exhibited unexplained Charcot-Marie-Tooth neuropathy was identified and designated pedigree K1550 (see Street et al., *Am J. Hum. Genet.* 70:244-250 (2002)). Another four generation family of English descent with 38 family members also comprising some family members exhibiting unexplained Charcot-Marie-Tooth neuropathy was identified and designated pedigree K1551. Id. Affected family members met widely accepted criteria for CMT1 disease including distal muscle weakness and atrophy, depressed deep tendon reflexes and sensory impairment (see Dyck and Lambert, *Arch. Neurol.* 18:603-618 (1968)). The mean ulnar (16.7 m/s [n=3], 25.3 [n=8]), median (23 m/s [n=5], 25.8 m/s [n=12]) and peroneal (20.4 m/s [n=4, 21 m/s [n=6]) motor nerve conduction velocities of affected K1550 and K1551 patients were consistent with CMT1 (see Street et al., *Neurology* 60:22-26 (2003)). One affected individual in pedigree K1550 had a sural nerve biopsy taken during reconstructive foot surgery that demonstrated "onion-bulb hypertrophy" typical of demyelinating CMT. Id. 200 unrelated control DNA samples for mutational analysis were taken from a collection of predominantly Caucasians of European descent.

Mapping and Identification of SIMPLE as a Candidate for CMT1:

To identify the locus responsible for the phenotype in these families, a whole genome-wide scan was performed in pedigrees K1550 and K1551, with informative microsatellite markers spaced at 10 cM intervals using the methods as described in Street et al., *Am. J. Med. Genet.* 70:244-250 (2002). Using two markers, D16S764 and D16S519 (obtained from Research Genetics), the CMT1 gene was mapped to chromosome 16p within a 9-cM interval. Id. SIMPLE was identified as one of 20 candidate genes that mapped to the critical region on chromosome 16p and was evaluated for DNA sequence alterations in families K1550 and K1551 (Street et al., *Neurology* 60:22-26 (2003)).

Molecular Analysis:

The following protocol of informed consent was approved by the institutional review board (IRB) of the University of Washington, Seattle. 15 to 20 mL of blood was obtained by venipuncture for high-molecular weight DNA (as described by Neitzel et al., *Hum. Genet.* 73:320-326 (1986)) and used as a template for PCR amplification. The three coding exons of the SIMPLE gene were PCR amplified from subject genomic DNA utilizing primer pairs listed in Table 2. PCR reactions were carried out in 25 µl containing 1×PCR buffer of 10 mM Tris-HCL (pH 8.3 at 25° C.), 50 mM KCL, 2 mM $MgCl_2$, 0.2 mM each dNTP (dATP, dCTP, dGTP, dTTP), 0.66 µM each oligonucleotide forward and reverse primer, and 0.6 U of 5 U/µl Ampli-Taq Polymerase (Sigma, St. Louis, Mo.). 5 µl of PCR product was characterized by gel electrophoresis/ethidium bromide staining for the presence of a single correctly sized band, as shown in Table 2.

Direct DNA Sequencing of the PCR Fragments:

5 µl of PCR product from each sample confirmed to have a single correctly sized band was treated with 1 µl of ExoSAP-IT (US Biochemical, Cleveland, Ohio) at 37° C. for 2 hours followed by heat inactivation at 85° C. for 10 minutes. Direct DNA sequencing of the purified fragments was carried out by using a BigDye Terminator Cycle Sequencing Ready Reaction Kit (Applied Biosystems Inc., Foster City, Calif.). The primers used for sequencing are the same primers used for PCR amplification as listed in Table 2. For initial mutation screening, either forward or reverse primer was used. The PCR reaction contained 3 µl of treated PCR product (~100 ng), 3 pmol primer, 1 µl sequencing buffer and 2 µl of BigDye reagent in a total volume of 10 µl. The sequencing reaction was carried out in a PTC-100 Programmable Thermal Controller (MJ Research Inc., Waltham, Mass.) with cycle conditions of 96° C. for 2 min, 30 cycles of 96° C. for 15 sec, 50° C. for 10 sec, and 60° C. for 4 min. The sequencing product was purified by ethanol/EDTA precipitation, then electrophoresed on an ABI DNA Sequencer (Applied Biosystems Inc., Foster City, Calif.).

Results:

Analysis of the three SIMPLE coding exons and flanking intron nucleotide sequences in pedigrees K1550 and K1551 revealed mutations in exon 3. In K1550, a C to A transversion at nucleotide 344 (as counted from the cDNA start codon as shown in SEQ ID NO: 1) was detected in exon 3, which predicts substitution of asparagine for threonine at amino acid position 115 (T115N).

In K1551, a G to A transition at nucleotide 344 was detected in exon 3, which predicts substitution of serine for glycine at amino acid position 112 (G112S).

Evaluation of Co-Segregation of CMT1C and Genetic Mutations

The C to A transversion at nucleotide 344 and the G to A transition at nucleotide 334 each introduced a novel BsrI restriction endonuclease site which was utilized to verify that the mutation co-segregates with subjects exhibiting peripheral neuropathy as further described in Example 3 and Table 4.

Example 2

This example describes the identification of the W116G missense mutation in the SIMPLE gene.

Subjects Tested:

A family of Dutch descent comprising 17 family members, some of which exhibited unexplained Charcot-Marie-Tooth neuropathy was identified and designated pedigree K2900 (see Street et al., *Neurology* 60:22-26 (2003)). The proband in this family had decreased nerve conduction velocities ranging from 15 to 30 m/s, consistent with CMT1C. Affected family members had previously been evaluated and shown not to have alterations in the PMP22, MPZ or EGR2 genes. 100 unrelated control chromosomes were also included in the study.

Methods:

The entire coding region of SIMPLE was sequenced in genomic DNA of one affected individual by first PCR amplifying the 3 coding exons (exons 2-4) and sequencing each using the primers shown in Table 2 as described in Example 1.

Results:

In K2900, a T to G transversion at nucleotide 346 (as counted from the cDNA start codon as shown in SEQ ID NO: 1) was detected in exon 3, which predicts substitution of glycine for tryptophan at amino acid position 116 (W116G).

Evaluation of Co-Segregation of CMT1C and Genetic Mutations

The T to G transversion at nucleotide 346 introduced a novel Nci1 restriction endonuclease site which was utilized to verify that the mutation co-segregates with subjects exhibiting peripheral neuropathy as further described in Example 3 and Table 4.

Example 3

This example describes the use of restriction fragment length polymorphism (RFLP) analysis to evaluate co-segregation of peripheral neuropathy with genetic mutation in the SIMPLE gene.

Of the 15 samples from individuals not exhibiting peripheral neuropathy, all Bsr1 restriction patterns corresponded to the expected fragment pattern for wild-type shown in Table 4. The expected wild-type fragment pattern was observed in 200 unrelated samples of control chromosomes.

T115N Mutation:

RFLP analysis was performed on samples from 29 individuals from the K1550 pedigree (described in Example 1), including 21 individuals exhibiting peripheral neuropathy. Bsr1 digestion of the 380 bp exon 3 fragment resulted in the pattern shown in Table 4 for mutant-type samples in all 21 subjects exhibiting peripheral neuropathy. Of the 8 samples from individuals not exhibiting peripheral neuropathy, all Bsr1 restriction patterns corresponded to the expected fragment pattern for wild-type shown in Table 4. The expected wild-type fragment pattern was observed in 200 unrelated samples of control chromosomes.

W116G Mutation:

RFLP analysis was performed on samples from 8 individuals from the K2900 pedigree (described in Example 2), including 4 individuals exhibiting peripheral neuropathy. Nci1 digestion of the 380 bp exon fragment resulted in the pattern shown in Table 4 for mutant-type samples in all 4 individual subjects exhibiting peripheral neuropathy. Of the 4 samples from individuals not exhibiting peripheral neuropathy, all Nci1 restriction patterns corresponded to the expected fragment pattern for wild-type shown in Table 4. The expected wild-type fragment pattern was observed in 100 unrelated samples of control chromosomes.

TABLE 4

THE CONDITIONS OF RFLP ANALYSIS FOR DETERMINING COSEGREGATION WITH DEMYELINATING NEUROPATHY

| Mutation | Primer Set | Enzyme | Restriction Fragment Sizes (bp) | | Conditions | |
|---|---|---|---|---|---|---|
| | | | Wild-type | Mutant | Temp | Buffer |
| 334G to A (G112S) | 3F (SEQ ID NO: 18) 3R (SEQ ID NO: 19) | Bsr1 | 380 | 121, 259 | 65° C. | NEBuffer 3 |
| 344C to A (T115N) | 3F (SEQ ID NO: 18) 3R (SEQ ID NO: 19) | Bsr1 | 380 | 108, 272 | 65° C. | NEBuffer 3 |
| 346T to G (W116G) | 3F (SEQ ID NO: 18) 3R (SEQ ID NO: 19) | Nci1 | 380 | 104, 276 | 37° C. | NEBuffer 4 |

Restriction Fragment Length Polymorphism (RFLP) Analysis:

Each of the identified mutations, G112S, T115N and W116G, alter the restriction endonuclease digestion pattern of specific restriction endonucleases as shown in Table 4. The first column of Table 4 describes the mutations amenable to RFLP analysis, the second column provides a useful primer set for amplification of the region encompassing the mutation, the third column provides the relevant restriction endonuclease for use in digestion of the PCR fragment, and the fourth and fifth columns provide the expected restriction enzyme digested fragments for wild-type and mutant genes, respectively. The final two columns of Table 4 provide the reaction conditions appropriate for each restriction enzyme digestion listed.

Results of Segregation Analysis:

G112S Mutation:

RFLP analysis was performed on samples from 33 individuals from the K1551 pedigree (described in Example 1), including 18 individuals exhibiting demyelinating peripheral neuropathy. Bsr1 digestion of the 380 bp exon 3 fragment resulted in the pattern shown in Table 4 for mutant-type samples in all 18 subjects exhibiting peripheral neuropathy.

Example 4

This example describes the analysis of SIMPLE gene expression after nerve injury in a rat model.

Methods:

Young adult Sprague-Dawley rats were anesthetized and the sciatic nerves were transected at the sciatic notch, and both cut ends were ligated and pulled apart to prevent axonal regeneration into the distal stump. The entire distal nerve stump (about 4 cm in length) was harvested during the next 1 to 58 days later and divided into 2-cm segments, termed P (the segment immediately adjacent to the crush) and D (the more distal segment). Further description of this experimental method is provided in Scarlato et al., *J Neurosci. Res.* 66:16-22 (2001).

RNA Expression Analysis:

RNA Isolation:

RNA was isolated by $CsCl_2$ gradient centrifugation as described by Chirgwin et al., *Biochem.* 18:5294-5299 (1979). For the lesioned adult rat sciatic nerves, total RNA was isolated from distal stumps of sciatic nerves that were transected or crushed and a Northern Blot was probed with the following cDNAs: a 1.4 kb fragment of SIMPLE, a full-length cDNA of rat myelin protein zero; and a full-length cDNA of rat GAPDH.

Results:

Northern blot analysis indicated that the 2.4 kb SIMPLE message was present at moderate levels in rat sciatic nerve, with expression remaining constant during sciatic nerve development. Following axotomy of transected sciatic nerve, SIMPLE expression remained essentially constant for a 48 day time course. Following crush injury, a general increase in SIMPLE expression was observed over a 58 day time course, and was more pronounced in the nerve region proximal to the site of injury. The fact that SIMPLE expression was unchanged as a result of nerve injury stands in distinct contrast to other CMT1 genes such as MPZ, PMP22, connexin-32 and EGR2, all of which have been found to demonstrate altered expression as a result of nerve injury (see Sherer et al., *J. Neurosci.* 15:8281-8294 (1995); Snipes et al., *J. Cell. Biol.* 117:225-238 (1992) and Zorick et al., *Mol. Cell. Neurosci.* 8:129-145 (1996)).

Protein Expression:

Blood samples were cleared of red blood cells by lysis in osmotic buffer (PureGene). Intact lymphocytes remaining in the lysate were then pelleted by centrifugation, washed in phosphate-buffered saline, and lysed in boiling SDS-PAGE loading buffer. 50 µg of each extract was resolved on a SDS-PAGE gel and transferred to PVDF membrane. Blots were then incubated with anti-LITAF monoclonal antibodies (Transduction Labs; 1:5000), followed by horseradish peroxidase-conjugated goat anti-mouse antibodies (Sigma; 1:20, 000). Detection was performed with the ECL Plus system (Amersham).

Results:

Western blot analysis of peripheral blood lymphocytes indicated that the T115N and W116G substitutions do not appear to alter the SIMPLE protein level compared to a control individual and an individual carrying the PMP22 duplication. This result is in contrast to the observation that overexpression of the PMP22 gene in CMT1A is associated with demyelination and formation of perinuclear protein aggregates (Matsumami et al., *Nat. Genet.* 1:176-179 (1992)).

Example 5

This example describes a kit and method of use for identifying genetic mutations associated with peripheral neurological disease in a mammalian subject, and for determining susceptibility or presence of CMT1C in a test subject.

Methods Utilized:

PCR Amplification:

Carried out as described in Example 1

Direct Sequencing:

Carried out as described in Example 1

Data Analysis:

The resulting sequences are aligned with the known exon sequence using a multiple sequence alignment tool, Sequencher (Gene Codes Corporation, Ann Arbor, Mich.), in order to identify any nucleotide changes. Electrophergrams are also visually examined to detect heterozygous base changes that might be missed by Sequencher.

Confirmation of the Nucleotide Changes:

Once a nucleotide change is detected, the exon fragment encompassing the suspected mutation is subjected to PCR amplification and direct sequencing again, using both forward and reverse primers as shown in Table 2.

For familial cases, when the nucleotide change is confirmed, with consent, the available family members, including affected and at risk unaffected individuals, are tested to confirm that the mutation segregates with the disease. After appropriate consent for clinical testing is obtained, the test may also be used for presymptomatic diagnosis in at-risk individuals.

Contents of the SIMPLE Mutation Kit:
1. 10×PCR Buffer (100 mM Tris-HCL (pH 8.3 at 25° C.), 500 mM KCL, 20 mM MgCl2
2. dNTP mix: dATP, dCTP, dGTP, dTTP at 10 mM each (Sigma, St. Louis, Mo.)
3. Ampli-Taq DNA Polymerase (Sigma, St. Louis, Mo.)
4. Primers for amplification of each SIMPLE exon and the adjacent intronic sequences at 0.66 µM each (as shown in Table 2)
5. Exo-SAP-IT (US Biochemical, Cleveland, Ohio)
6. BigDye Terminator Cycle Sequencing Ready Reaction Kit (Applied Biosystems Inc., Foster City, Calif.)
7. Control DNA
8. Written instructions and indicia indicating a positive correlation between the presence of a particular mutation in the SIMPLE gene and the risk of CMT1C disease.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of identifying a genetic mutation in a human small integral membrane protein of the lysosome/late endosome ("SIMPLE") gene in a human subject, said method comprising:
   (a) hybridizing a nucleic acid sequence of a coding region of a human small integral membrane protein of the lysosome/late endosome ("SIMPLE") gene consisting of a coding portion of SEQ ID NO:1, or a naturally occurring sequence alteration thereof from a human subject with an oligonucleotide specific for a SIMPLE gene missense mutation, wherein the missense mutation alters the encoded amino acid sequence at a residue selected from the group consisting of amino acid residues 112, 115, and 116 of SEQ ID NO:2; and
   (b) detecting hybridization of the oligonucleotide with the nucleic acid sequence from the human subject; and
   (c) identifying a genetic mutation in the SIMPLE gene in the subject when hybridization is detected in step (b).

2. The method of claim 1, wherein the missense mutation is a dominant mutation.

3. The method of claim 1, wherein the missense mutation encodes an altered SIMPLE amino acid sequence at residue 112, resulting in G112S.

4. The method of claim 1, wherein the missense mutation an altered SIMPLE amino acid sequence at residue 115, resulting in T115N.

5. The method of claim 1, wherein the missense mutation encodes an altered SIMPLE amino acid sequence at residue 116, resulting in W116G.

* * * * *